United States Patent
Fontana et al.

(10) Patent No.: US 7,393,961 B2
(45) Date of Patent: Jul. 1, 2008

(54) POLYHALOGENATED ETHERS

(75) Inventors: Giovanni Fontana, Verona (IT); Walter Navarrini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

(21) Appl. No.: 11/073,581

(22) Filed: Mar. 8, 2005

(65) Prior Publication Data

US 2005/0148783 A1    Jul. 7, 2005

Related U.S. Application Data

(62) Division of application No. 10/357,364, filed on Feb. 4, 2003, now Pat. No. 6,936,722.

(30) Foreign Application Priority Data

Feb. 5, 2002    (IT) ................ MI2002A0198

(51) Int. Cl.
C07D 307/02 (2006.01)
C07C 59/21 (2006.01)

(52) U.S. Cl. .............. 549/252; 549/231; 568/614; 568/615; 558/15; 558/16; 558/53; 558/204; 558/260; 558/300; 558/301; 560/183; 560/263; 562/849; 564/32

(58) Field of Classification Search ............ 568/614, 568/615
See application file for complete search history.

(56) References Cited

U.S. PATENT DOCUMENTS

| | | | |
|---|---|---|---|
| 2,500,388 A * | 3/1950 | Simons ............... 568/683 |
| 3,114,778 A | 12/1963 | Gerhard et al. |
| 3,175,378 A | 3/1965 | Russell |
| 3,250,806 A | 5/1966 | Warnell ............... 260/535 |
| 3,683,027 A | 8/1972 | Sianesi et al. |
| 3,692,843 A * | 9/1972 | Resnick ............... 568/598 |
| 3,847,978 A | 11/1974 | Sianesi et al. |
| 4,460,514 A | 7/1984 | Baucom et al. |
| 4,499,024 A | 2/1985 | Fifolt |
| 4,570,004 A | 2/1986 | Lagow et al. |
| 4,675,452 A | 6/1987 | Lagow et al. ............... 568/601 |
| 4,720,527 A | 1/1988 | Caporicio et al. ........... 525/403 |
| 4,801,409 A | 1/1989 | Marraccini et al. |
| 4,827,024 A | 5/1989 | Guglielmo et al. |
| 4,900,872 A | 2/1990 | Guglielmo et al. |
| 4,906,770 A | 3/1990 | Marchionni et al. |
| 5,143,589 A | 9/1992 | Marchionni et al. |
| 5,149,842 A | 9/1992 | Sianesi et al. |
| 5,225,576 A | 7/1993 | Navarrini et al. |
| 5,258,110 A | 11/1993 | Sianesi et al. |
| 5,488,181 A | 1/1996 | Marchionni et al. |
| 5,877,357 A | 3/1999 | Marraccini et al. |
| 6,127,498 A | 10/2000 | Tonelli et al. |
| 6,255,536 B1 * | 7/2001 | Worm et al. ............... 568/615 |

FOREIGN PATENT DOCUMENTS

| | | |
|---|---|---|
| EP | 0 194 862 A | 9/1986 |
| EP | 0 201 871 A | 11/1986 |
| EP | 201871 | * 11/1986 |
| EP | 0 267 626 A | 5/1988 |
| EP | 0 267 627 A | 5/1988 |
| EP | 0 460 948 A | 12/1991 |
| EP | 0 683 181 | 5/1995 |
| EP | 0 754 670 | 1/1997 |
| GB | 1 104 482 | 4/1965 |
| GB | 1 189 337 | 7/1967 |
| IT | 20000MI1844 | * 2/2002 |
| JP | 58-164535 | * 9/1983 |
| WO | WO 90/03409 | 4/1990 |
| WO | WO 94/13612 | 7/1994 |

OTHER PUBLICATIONS

Brice and Coon, "The Effects of Structure on the Viscosities of Perfluoroalkyl Ethers and Amines" Journal of the American Chemical Society, vol. 75, pp. 2921-2925 (1953).*

"Electrochemical Fluorination of 1,4-Dioxane and Other Ethers of Ethylene Glycol", Berenblit et al, *J. Appl. Chem.* USSR, vol. 53, No. 4, 1980, pp. 673-675.

"Successful Direct Fluorination of Oxygen-Containing Hydrocarbons", Adcock et al, *J. Org. Chem.*, vol. 40, No. 22, 1975, p. 3271-3275.

"Synthesis of Perfluoropoly (ethylene glycol) Ethers by Direct Fluorination", Gerhardt et al, *J. Org. Chem.*, vol. 43, No. 23, 1978, pp. 4505-4509.

Database Crossfire Beilstein 'Online! Beilstein Institut zur Forderung der Chemischen Wissenschaften, Frankfurt am Main, DE, Database accession No. 6211879 XP002239261 & Brace, *J. Fluorine Chem.*, vol. 18, 1981, pp. 515-524.

Database Caplus 'Online! Chemical Abstracts Service, Columbus, Ohio, Database Accession No. 116:105755 XP002239262 & "The Synthesis of Perfluoroalkyl and Perfluoroalkyl Ether Substituted Benzils", Paciorek et al, *J. Fluorine Chem.*, vol. 53, No. 2, 1991, pp. 233-248.

Database Caplus 'Online! Chemical Abstracts Service, Columbus, Ohio, Database Accession No. 109:149500 XP002239263 & "Synthesis of Perfluoro Crown Ethers: A New Class of Cyclic Fluorocarbons", Lin et al, *Pure and Applied Chemistry*, vol. 60, No. 4, 1988, pp. 473-476.

Database Caplus 'Online! Chemical Abstracts Service, Columbus, Ohio, Database Accession No. 79:91514 XP002239264 & "Preparation of Highly Fluorinated Ethers", De Pasquale, *J. Org. Chem.*, vol. 38, No. 17, 1973, pp. 3025-3030.

Database Caplus 'Online! Chemical Abstracts Service, Columbus, Ohio, Database Accession No. 96:6134 XP002239265 & "Some Approaches to the Synthesis of Fluorinated Alcohols and Esters. I. Completely Fluorinated Esters from the Hunsdiecker Reaction of Silver Perfluoroalkanoates with Iodine", Brace, *J. Fluorine Chem.*, vol. 18, No. 4-6, 1981, pp. 515-524.

(Continued)

*Primary Examiner*—Rosalynd Keys
(74) *Attorney, Agent, or Firm*—Arent Fox LLP

(57) ABSTRACT

(Per)haloethers having formula:

$$X-(Rf)_L-O-CF_2CF_2-O-CX_1X_2-CFX_3X_4, \quad (I)$$

process for obtaining them and hypofluorites usable in the synthesis of said (per)haloethers.

20 Claims, No Drawings

OTHER PUBLICATIONS

Database WPI, Section Ch, Week 199107, Derwent Publications Ltd., London, GB, AN 1991-047261 XP002239267 & JP 02-311436 A, Dec. 27, 1990.

Database Crossfire Beilstein 'Online! Beilstein Institut zur Forderung der Chemischen Wissenschaften, Frankfurt am Main, DE, Database Accession No. 2358915 XP002239266 & "Introduction of Functional Groups into Some Chlorofluorocarbon Ethers", Schack et al, *J. Fluorine Chem.*, vol. 14, No. 6, 1979, pp. 519-522.

Adv. Flourine Chem. 7 (1973), 175-198.

Ruff J. K. et al., J. Am. Chem. Soc. 88:19 (1966), pp. 4531-4532.

Riley et al., "The synthesis of fluoroether-fluorosilicone hybrid polymers", J. Fluorine Chem., vol. 10, 1977, pp. 85-110.

Lustig et al., J. Am. Chem. Soc. 89-12 (1967), pp. 2841-2843.

Hohorst A., et al., J. Am. Chem. SOc. 89:9 (1967), pp. 1809-1810.

\* cited by examiner

POLYHALOGENATED ETHERS

CROSS-REFERENCE TO RELATED APPLICATION

This application is a divisional application which claims the benefit of application Ser. No. 10/357,364, filed Feb. 4, 2003 now U.S. Pat. No. 6,936,722. The disclosure of the prior application is hereby incorporated herein by reference in its entirety.

The present invention relates to (per)haloethers, the process for their preparation and perfluorooxyalkyl hypofluorites usable in the synthesis of said (per)haloethers.

It is generally stated in the prior art that (per)haloethers, obtained by reacting perfluoroalkyl hypofluorites with (per) halo-olefins, can be used as such or for the preparation of perfluorovinylether monomers. See for example patents U.S. Pat. No. 5,877,357 and EP 683,181. Said monomers are usable in the fluoroelastomer and fluoroplastomer synthesis.

The reaction between the hypofluorite and a (per)haloolefin for the preparation of (per)haloethers is carried out by flowing a gaseous phase, containing the hypofluorite, in the liquid phase containing the (per)halo-olefin at low temperature. See U.S. Pat. No. 5,225,576. To obtain high yields of the sum reaction, it is necessary to work at low temperature. There is however the drawback that an even partial condensation of the hypofluorite can take place before it comes into contact with the olefin. This leads to the hypofluorite decomposition and therefore it can lead to violent explosions. For example, the hypofluorite $CF_3CF_2CF_2OF$ having molecular weight 204 has a boiling point of $-9°$ C. (Journal of fluorine Chemistry, Vol. 95 (1999) 29) and it can easily condensate at the temperatures used in the (per)haloether synthesis. At temperatures lower than $-30°$ C. the process of the above patent is applicable only to hypofluorites having a low boiling point, i.e., having 1 or 2 carbon atoms in the chain.

Alternatively to the above process, it is known in the prior art that (per)haloethers can be obtained by dissolving the hypofluorite in a suitable halogenated solvent and by adding the solution to the (per)halo-olefin, as for example described in U.S. Pat. No. 4,900,872. From the Examples of said patent the yields are high when perfluoroalkylhypofluorites having in the chain two carbon atoms are used as hypofluorites. When 1-chloroperfluoroethyl hypofluorite is used, the yields are lower than 30%. Hypofluorites different from (per)fluoroethyl hypofluorites having two carbon atoms are not exemplified. Besides, according to the teaching of said patent, the hypofluorite is synthesized in gaseous phase at low temperature and subsequently is dissolved in an inert solvent up to a concentration of 50% by weight at most.

U.S. Pat. No. 4,906,770 describes hypofluorites of formula $Rf^1OCF_2OF$ and $FOCF_2ORf^1OCF_2OF$, wherein $Rf^1$ is a perfluoropolyether radical even having a high molecular weight, and the respective addition products with olefins. The process for preparing said hypofluorites includes a peroxide fluorination reaction with UV light at tempertures between $-60$ and $30°$ C. From the Examples the reaction times are very high. The conversions to hypofluorite, when they are complete, determine low hypofluorite yields. Besides the use of the UV light is expensive in an industrial process.

Patent application EP 754,670 describes hypofluorites of formula $FC(O)-Rf^2-CF_2OF$, wherein $Rf^2$ is a $(C_1-C_{12})$ perfluoroalkyl or perfluorooxyalkyl chain having molecular weight in the range 100-2,000. The Examples of said patent relate to the hypofluorite synthesis and the sum reaction with olefins is never mentioned. The Applicant has shown, see the comparative Examples, that by using the compounds $CF_3CF_2CF_2$—OF and $CF_3O$—$CF(CF_3)$—$CF_2OF$, which have a structure similar to the products of said Examples, the yields of the addition reaction with fluoroolefins are very low.

U.S. Pat. No. 4,827,024 describes $C_1$-$C_{20}$ fluoroalkyl or oxyfluoroalkyl hypofluorites. No Example of addition of the hypofluorite to the olefin is mentioned. Among the exemplified compounds there are hypofluorites having more than two carbon atoms. The Applicant has shown that said hypofluorites give the sum reaction with (per)halo-olefins with very low yields (see comparative Examples).

U.S. Pat. No. 4,801,409 describes the preparation of bis hypofluorites of general formula $FOCF_2-Rf^3-CF_2OF$ in gaseous phase. $Rf^3$ is a perfluoroalkylene or perfluorooxyalkylene. The sole reported Example of hypofluorite having a number of carbon atoms higher than two is hypofluorite having three carbon atoms. Tests carried out by the Applicant have shown that with said hypofluorites very low yields of addition to olefins are obtained.

From the prior art the hypofluorite synthesis with a number of carbon atoms higher than two is carried out at temperatures from 0° C. to 60° C., in particular at 20° C. in gaseous phase to avoid possible condensation risks and therefore explosions. Furthermore one works at very high dilutions of the acylfluoride precursor. See U.S. Pat. No. 4,801,409.

The technical problem that the present invention intends to solve refers to the synthesis with high yields of (per)haloethers, wherein hypofluorites having a number of carbon atoms higher than 2 are used. The data reported in the prior art relating to the use of (per)fluoroalkyl hypofluorites having a number of carbon atoms higher than two are very poor and anyhow they give very low yields of addition to olefins (see comparative Examples). This is due to the fact that said compounds cause explosions and are difficult to handle. See U.S. Pat. No. 4,900,872.

As a matter of fact it is known that linear perfluoroalkyl hypofluorites having a number of carbon atoms higher than two have poor stability and tend to decompose very easily even with very violent reactions. See for example Adv. Fluorine Chem. 7 (1973) 175-198; Explosive Incident report N° 189, Armed Services Safety Board, Washington, D.C.; Chem. & Engin. 1 Mar. 1965.

The need was felt to have available (per)haloethers obtainable from hypofluorites having a number of carbon atoms higher than two by a process having high yields and without explosion danger, utilizing hypofluorites even having a high molecular weight. Said (per)haloethers are usable for the preparation of (per)fluorovinylether monomers, which as known, are highly required in the preparation of fluoropolymers, for example elastomeric fluoropolymers.

An object of the present invention are (per)haloethers having formula (I)

$$X\text{-}(Rf)_L\text{-}O\text{---}CF_2CF_2\text{---}O\text{---}CX_1X_2\text{---}CFX_3X_4 \qquad (I)$$

wherein:

$X_1, X_2, X_3, X_4$ have the following meanings:
1) independently each from the other, they are F, H, Cl or Br; preferably F, H, Cl; more preferably.:
   $X_3=F$ and $X_4=Cl$, $X_1=F$ and $X_2=Cl$;
   $X_3=F$ and $X_4=Cl$, $X_1=F$, $X_2=H$;
   $X_1=X_3=H$ and $X_2=X_4=Cl$;
   $X_1=X_3=X_4=Cl$ and $X_2=H$;
2) one of $X_1$ or $X_2$, and/or one of $X_3$ or $X_4$, is/are chosen from the following groups: —$COOR^1_H$, wherein $R_{1H}$ is $C_1$-$C_3$ alkyl; —$OC(O)CH_3$; —CN; —NCO; —NCS; aryl, substituted and non substituted, when substituted the substituent is $NO_2$; —NH—C(O)—$NH_2$; —OC(O)

$_2CH_3$; —$P(O)(C_6H_5)_2$; —$P(O)_2(C_6H_5)_2$; —$SO_2F$; preferably the groups are the following: —$COOR^1_H$, —CN, NCO, NCS, aryl as above defined, —$SO_2F$;
whereas the remaining substituents of the group of $X_1$ $X_2$, $X_3$, $X_4$ have the meanings as defined under 1);
3) one of $X_1$ or $X_2$, and/or one of $X_3$ or $X_4$, is/are chosen from the following groups:
3)a. $C_1$-$C_{20}$, preferably $C_1$-$C_5$, linear or branched per (halo)fluorinated alkyl, preferably (per)fluoroalkyl;
3)b. $C_1$-$C_{20}$, preferably $C_1$-$C_5$, linear or branched per (halo)fluorinated oxyalkyl, preferably (per)fluorooxyalkyl;
wherein when the alkyl is per(halo), there are one or more atoms of Cl and/or Br;
3)a. and 3)b. preferably each contain one or more functional groups chosen from those indicated in 2) and/or from fluorinated or hydrogenated organic anhydrides chosen from the group of linear anhydrides of organic $C_1$-$C_4$ mono-carboxylic acids or cyclic anhydrides of $C_4$-$C_6$ dicarboxylic acids, within the anhydrides preferably cyclic anhydrides of $C_4$-$C_6$ dicarboxylic acids;
3)c. $C_1$-$C_{10}$, preferably $C_1$-$C_5$, linear or branched alkyl, optionally containing one or more functional groups, chosen between those indicated above under 3), excluding fluorinated organic anhydrides;
wherein the remaining substituents of the group of $X_1$, $X_2$, $X_3$, $X_4$ have the meanings as defined under 1);
4) one of $X_1$ or $X_2$, together with one of $X_3$ or $X_4$ and the two carbon atoms of the group —$CX_1X_2$—$CFX_3X_4$ form cyclic fluorinated or hydrogenated anhydride or imide compounds, containing in the ring 4-6 carbon atoms, preferably 4 carbon atoms,
wherein the remaining substituents between $X_1$ or $X_2$, and between $X_3$ or $X_4$, have the meanings as defined under 1);
4a) $X_3$ and $X_4$, together with the relevant carbon atom to which they are attached, form a cyclic anhydride ring having 4 carbon atoms; $X_1$ and $X_2$ have the meanings as defined under 1);
X has the following meanings:
F, linear or branched $C_1$-$C_3$ per(halo)alkyl; preferably (per)fluoroalkyl, wherein optionally one fluorine atom is substitued with one chlorine atom; —$[O]_T CF_2CF_2OCX_1X_2$—$CFX_3X_4$, —$[O]_T CF_2C(O)F$,
wherein
T=0 when L=1 and Rf=Rf" as defined below;
T=0 when L=0;
T=1 when L=1 and Rf=Rf' as defined below;
when L=1 and Rf=Rf' as defined below, X can be also a $C_1$-$C_5$ perfluoroxyalkyl;
L=0, 1;
when L=0, from the X meanings the following are excluded:
F;
—$[O]_T CF_2CF_2OCX_1X_2$—$CFX_3X_4$ being T=0, $X_1$=F, $X_2$=Cl, $X_3$=F, $X_4$=Cl;
$C_1$-$C_3$ perfluoroalkyl when $X_1$=F, $X_2$=Cl, $X_3$=F and $X_4$=Cl;
when L=1, Rf=Rf' or Rf"; being
Rf'=$C_1$-$C_{20}$ perfluoroalkylene;
Rf"=perfluorooxyalkylene having formula:

$$-(OCF_2CF_2)_m(OCF_2)_n(OCF_2CFCF_3)_p(OCFCF_3)_q(OCF_2CF_2CF_2)_r- \quad (V)$$

wherein m, n, p, q, r are integers such that:
m is comprised between 0 and 100, extremes included;
n is comprised between 0 and 100, extremes included;
p is comprised between 0 and 60, extremes included.;
r is comprised between 0 and 60, extremes included;
q is comprised between 0 and 60, extremes included;

$$m+n+p+r+q \geq 1;$$

the number average molecular weight of Rf" being from 66 to 12,000 preferably from 66 to 3,000.
Preferably when Rf=Rf", the perfluorooxyalkylene has the following formula:

$$-(OCF_2CF_2)_m(OCF_2)_n- \quad (VI)$$

wherein m and n independently from each other have the above values, preferably from 0 to 20; when both m and n are present, m/n ranges from 0.1 to 6.
The preferred (per)haloethers of formula (I) are the following:

$CF_3CF_2O$—$CF_2CF_2$—O—$CHCl$—$CFCl_2$;
$CF_3OCF_2O$—$CF_2CF_2$—O—$CFCl$—$CF_2Cl$;

$CF_3OCF_2CF_2O$—$CF_2CF_2$—O—$CFCl$—$CF_2Cl$;

$CF_3OCF_2OCF_2O$—$CF_2CF_2$—O—$CFCl$—$CF_2Cl$;

$CF_3O$—$CF_2CF_2$—O—$CHCl$—$CHFCl$; $CF_3O$—$CF_2CF_2$—O—$CHCl$—$CFCl_2$;

$CF_3CF_2O$—$CF_2CF_2$—O—$CHCl$—$CHFCl$;

$CF_3OCF_2O$—$CF_2CF_2$—O—$CHCl$—$CHFCl$; $CF_3O$—$CF_2CF_2$—O—$CHCl$—$CFCl$;

$CF_3OCF_2O$—$CF_2CF_2$—O—$CHCl$—$CHFCl$;

$F(O)CCF_2$—O—$CF_2CF_2$—O—$CFCl$—$CF_2Cl$; $F(O)CCF_2$—O—$CF_2CF_2$—O—$CHCl$—$CHFCl$;

$F(O)CCF_2$—$OCF_2O$—$CF_2CF_2$—O—$CFCl$—$CF_2Cl$;

$F(O)CCF_2$—$OCF_2O$—$CF_2CF_2$—O—$CHCl$—$CFCl_2$;

$F(O)CCF_2$—$OCF_2CF_2O$—$CF_2CF_2$—O—$CFCl$—$CF_2Cl$;

$F(O)CCF_2$—$OCF_2OCF_2CF_2O$—$CF_2CF_2$—O—$CFCl$—$CF_2Cl$;

$F(O)CCF_2$—$OCF_2CF_2OCF_2O$—$CF_2CF_2$—O—$CFCl$—$CF_2Cl$;

$CHFClCHClO$—$CF_2CF_2$—O—$CF_2CF_2$—O—$CHCl$—$CHFCl$;

$CF_2ClCFClO$—$CF_2CF_2$—$OCF_2O$—$CF_2CF_2$—O—$CFCl$—$CF_2Cl$;

$CF_2ClCFClO$—$CF_2CF_2$—$OCF_2CF_2O$—$CF_2CF_2$—O—$CFCl$—$CF_2Cl$;

$CF_2ClCFClO$—$CF_2CF_2$—$OCF_2OCF_2CF_2O$—$CF_2CF_2$—O—$CFCl$—$CF_2Cl$;

$CFCl_2CHClO$—$CF_2CF_2$—O—$CF_2CF_2$—O—$CHCl$—$CFCl_2$;

$CFCl_2CHClO$—$CF_2CF_2$—$OCF_2O$—$CF_2CF_2$—O—$CHCl$—$CFCl_2$;

$CFCl_2CHClO$—$CF_2CF_2$—$OCF_2CF_2O$—$CF_2CF_2$—O—$CHCl$—$CFCl_2$;

$CFCl_2CHClO$—$CF_2CF_2$—$OCF_2OCF_2CF_2O$—$CF_2CF_2$—O—$CHCl$—$CFCl_2$;

$CF_3O—(CF_2CF_2O)_m(CF_2O)_n—CF_2C(O)F;$ $CF_3CF_2O—(CF_2CF_2O)_m(CF_2O)_n—CF_2C(O)F;$ $CF_3CF_2CF_2O—(CF_2CF_2O)_m(CF_2O)_n—CF_2C(O)F;$ $(CF_3)_2CFO—(CF_2CF_2O)_m(CF_2O)_n—CF_2C(O)F;$ $CF_3O—(CF_3)CFO—(CF_2CF_2O)_m(CF_2O)_n—CF_2C(O)F;$ $CF_3O—(CF_2CF_2O)_m(CF_2O)_n—CF_2CF_2OCH_2CF_3;$ $F(O)CCF_2O—(CF_2CF_2O)_m(CF_2O)_n—CF_2CF_2OCH_2CF_3;$ $F_3CCH_2OCF_2CF_2O—(CF_2CF_2O)_m(CF_2O)_n—CF_2CF_2OCH_2CF_3;$ $CF_3O—(CF_2CF_2O)_m(CF_2O)_n—CF_2CF_2OCH_2CHFCOOMe;$ $F(O)CCF_2O—(CF_2CF_2O)_m(CF_2O)_nCF_2—CF_2OCH_2CHFCOOMe;$ $MeOCOCHFCH_2OCF_2CF_2O—(CF_2CF_2O)_m(CF_2O)_n—CF_2CF_2OCH_2CHFCOOMe;$

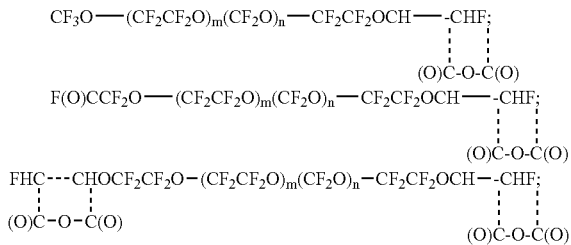

wherein: $m/n=4.3$ and MW of the perfluorpolyether chain $—(CF_2CF_2O)_m(CF_2O)_n—$ is 620.

The invention products of formula (I) are usable for the preparation of vinylethers, when at least two end carbon atoms are dehalogenable or dehydrohalogenable. Therefore the substituent groups $X_1$, $X_2$, and respectively $X_3$ and $X_4$ of the carbon atoms in terminal position of the (per)haloether, must be such that it is possible to carry out a dehalogenation or dehydrohalogenation. This preferably takes place when at least one of $X_1$ or $X_2$ are H, Cl, Br and at least one of $X_3$ or $X_4$ is H, Cl, Br. For the dehalogenation one of $X_1$ or $X_2$ and respectively of $X_3$ or $X_4$ must be equal and selected between Cl and Br. For the dehydrohalogenation at least one of the substituents between $X_1$ and $X_2$ or between $X_3$ and $X_4$ is H, and at least one of the substituents $X_3$ or $X_4$ when H is $X_1$ or $X_2$, or $X_1$ and $X_2$ when H is $X_3$ or $X_4$, is Cl or Br. vinylethers can, therefore, be obtained from the formula (I) compounds, as said, having respectively the following end groups:

—$CF_2$—COF and the other end group unsaturated;
both end groups unsaturated;
one end group unsaturated and the other (per)haloalkylic.

As said, these products are used as vinylethers, in the polymerization of fluorinated monomers to give fluoropolymers.

When the substituents $X_1$, $X_2$, $X_3$, $X_4$ are such as not to be comprised in the above conditions, whereby it is not possible to carry out the dehalogenation or the dehydrohalogenation, the formula (I) products are used as additives for polymers, solvents, refrigerants, surfactants, etc. When at least one of $X_1$, $X_2$, $X_3$, $X_4$ is equal to H said products have a low environmental impact.

Furthermore when one operates with a partial fluorination of the starting diacylfluoride and subsequent addition of the formed hypofluorite to a perfluorinated or perfluoropolyether olefin the process of the invention allows to obtain monocarbonylic (per)fluorinated products. (See the Examples).

When the used olefins contain one or more functional groups as above described in 2) and 3), (esters, cyano, amides, —$SO_2F$, isocyanates, isothiocyanates, aryls, optionally substituted, anhydrides, phosphine oxides —$P(O)(C_6H_5)_2$ or phosphonates —$P(O)_2(C_6H_5)_2$ the obtained (per)haloether products can be used as surfactant compounds, for treatment of surfaces (oil and water repellents) and additives.

A further object of the present invention is a process for obtaining the formula (I) (per)haloethers, excluding only the case when L=0 X is different from F, comprising the following steps:

a) synthesis of the formula (II) hypofluorite $$X'\text{-}(Rf)_L\text{-}O—CF_2CF_2—OF \qquad (II)$$

wherein:
X' has the following meanings:
F, linear or branched $C_1$-$C_3$ per(halo)alkyl; preferably perfluoroalkyl, wherein optionally one fluorine atom is substituted with one chlorine atom; or
—$[O]_TCF_2CF_2OF$, —$[O]_TCF_2C(O)F$, wherein T=0 when Rf=Rf'' as above; T=1 when Rf=Rf' as above; T=0 when L=0;
L=0, 1;
when L=0 then X' is different from F and from —$CF_2$—$CF_2OF$;
when L=1 Rf=Rf' or Rf''; being Rf'=$C_1$-$C_{20}$ perfluoroalkylene and Rf''=perfluorooxyalkylene having formula (V) as above, more preferably having formula (VI) as above, the number average molecular weight of Rf'' being from 66 to 12,000;
when L=1 and Rf=Rf', X' is also $C_1$-$C_5$ perfluoroxyalkyl;
by fluorination of an acylfluoride of formula (III)

$$X'\text{-}(Rf)_L\text{-}O—CF_2—C(O)F \qquad (III)$$

wherein X', L and Rf have the above meanings, at temperatures between −100° and +50° C., preferably between −80° and +20° C., in the presence of a catalyst, or mixtures of catalysts, having general formula $MeF_y \cdot zHF$, wherein Me is an alkaline or alkaline-earth metal, or silver; y is 1 or 2, depending on the metal valence, z is zero or ranges from 0.5 to 4, preferably z=0 or 1;
in absence or in the presence of inert, liquid or gaseous diluents;

b) reaction of the hypofluorites (II) with (per)halo-olefins of formula $$CX_1X_2=CX_3X_4 \qquad (VII)$$

wherein $X_1$, $X_2$, $X_3$ and $X_4$ are as above, at a temperature in the range from 0° C. to 120° C., preferaably from −60° C. to −110° C., in absence or in the presence of inert, liquid or gaseous diluents.

Examples of olefins that can be used in the process of the present invention are for instance the following: CFCl=CFCl; CHCl=CHCl; CHCl=CCl$_2$; CH$_2$=CF$_2$; CFH=CFCl; CF$_2$=CF$_2$; CF$_2$=CF—CF$_3$; CF$_2$=CF—OCF$_3$; CF$_2$=CF—OCF$_2$CF$_3$; CF$_2$=CF—OCF$_2$CF$_2$CF$_3$; CF$_2$=CFOCF$_2$CF$_2$SO$_2$F, CF$_2$=CFOCF$_2$OCF$_2$C(O)F, CF$_2$=CFOCF$_2$OCF$_2$COOMe, methyl or ethyl esters of (met)

acrylic acids, $CH_2=CH-O-C(O)CH_3$; $CH_2=CH-CH_2-O-C(O)CH_3$, $CH_2=CH-CH_2-Ar$, $CH_2=CH-Ar$, $CH_2=CH-CN$, $CH_2=CH-CH_2COOMe$, $CH_2=CH-CH_2Cl$, dimethyl or diethyl esters of maleic or fumaric acid, maleic anhydride, itaconic anhydride.

The process according to the present invention can be carried out in a discontinous, semicontinuous or in a continuous way.

The discontinuous and semicontinuous processes imply the use of a sole reactor, wherein the fluorination and addition reactions (one pot reactions) are carried out.

When one operates in a discontinuous or semicontinuous way, in step b) preferably the olefin is added to the hypofluorite.

The continuous process implies the use of two separate reactors wherein the fluorination and the addition reaction to the olefin are respectively carried out.

With the processes in a discontinuous, semicontinuous and continuous way, preferably the hypofluorite concentration in the added inert, liquid or gaseous diluent, such as for example those mentioned below, is higher than 50% by weight, preferably higher than 70% by weight, still more preferably one works in absence of inert diluent, to avoid the above mentioned drawbacks of the prior art.

The fluorination reaction for preparing the hypofluorite step a) can be carried out in excess or in defect of fluorine with respect to the acylfluoride, at temperatures in the range from −100° to +50° C., preferably from −80° to +20° C., in absence or in the presence of a diluent inert under the reaction conditions. The diluents mentioned below, for example, $C_3F_8$, $C_4F_8$ (cycle), $C_3F_8O$(ether), $CF_3-(CF_2)_2-CF_3$, $N_2$, $CF_4$, $C_2F_6$, perfluoropolyethers, for example Galden® HT 55, can be used.

The formula (III) acylfluorides can be prepared by synthesis of the peroxidic raw product and subsequent reduction to obtain perfluoropolyether components having end acylfluorides. The peroxidic raw product synthesis is carried out by oxidative polymerization of fluoroolefins, in particular $C_3F_6$ and/or $C_2F_4$ with oxygen at low temperature, in the presence of UV light or of a radical initiator, as for example described in patents GB 1,189,337, GB 1,104,482, U.S. Pat. No. 3,683,027, U.S. Pat. No. 3,175,378, U.S. Pat. No. 5,149,842, U.S. Pat. No. 5,258,110, U.S. Pat. No. 5,488,181. The peroxidic raw product reduction is carried out with hydrogen in a suitable catalyst containing palladium to give perfluoropolyether products with acylfluoride end groups, for example as described in U.S. Pat. No. 3,847,978, U.S. Pat. No. 6,127,498. Alternatively perfluoropolyether products having acylfluoride end groups can be obtained by fluoroolefin photooxidation in the presence of a chain transfer agent as described in U.S. Pat. No. 5,143,589. Besides U.S. Pat. No. 4,460,514 describes the preparation of oligomers $(OCF_2)$ having $-OCF_2-COF$ end groups.

The acylfluorides are obtainable also by electrochemical fluorination of the corresponding carboxylic acids, according to known methods of the prior art. Said process is applicable also for the acylfluorides wherein Rf=Rf'.

The catalysts used in step a) are known in the prior art. U.S. Pat. No. 4,827,024, U.S. Pat. No. 4,499,024, EP 754,670, Ruff J. K. et Al., J. Am. Chem. Soc. 88: 19 (1966) pp. 4531-4532, Lustig et Al., J. Am. Chem. Soc. 89: 12 (1967) pp. 2841-2843; Hohorst A. et Al., J. Am. Chem. Soc. 89: 8 (1967) pp. 1809-1810 can be mentioned. As an example the following can be mentioned: LiF, NaF, KF, CsF, $KHF_2$, AgF. Said catalysts can be used as such or mixed among each other.

The fluorination reaction can be carried out at a pressure equal to or higher than the atmospheric pressure, for example up to 2 atmospheres, and it takes place with very short contact times. The conversion of the reactant in defect, with respect to the equimolar stoichiometry between acylfluoride equivalents and $F_2$ fluorine moles, is complete and the hypofluorite fluorination yield, calculated with respect to the reactant in defect, is very high, generally higher than 95%.

With inert diluents usable in the present invention process are meant liquid or gaseous compounds inert under the reaction conditions. In particular inert diluents, also usable in step b), are for example $C_3F_8$, $C_4F_8$cycle, $C_3F_8O$ (ether), (per)fluoropolyethers, for example Galden® HT 55 (perfluoropolyether solvent having b.p. 55° C.), α,ω-dihydrofluoropolyethers, preferably the boiling point of the (per)fluoropolyethers and α,ω-dihydrofluoropolyethers is in the range from 30° C. to 300° C., $CHCl_2-CF_3$, $CF_3-CH_2F$, $CF_3CF_2Cl$.

In the discontinuous process a single addition is made of the required amount of fluorine to the suspension containing the catalyst and acylfluoride, at the above temperatures from −80° C. to +20° C. The subsequent fluorination reaction takes place with total conversion of the acylfluoride. After elimination of the unreacted fluorine, the (per)haloolefin is added to the hypofluorite, in absence or in the presence of the above diluents, at temperatures preferably in the range from −110° C. to −60° C., to obtain the final (per)haloether component.

In the discontinuous process according to the present invention the two consecutive reactions of the acylfluoride fluorination and of the olefin addition to the hypofluorite, are carried out in a sole reactor, by alternating the fluorine feeding with that of the olefin. In the reactor the catalyst based on fluoride metal necessary in the first fluorination phase is always present. The catalyst used in the present invention process is inert under the conditions of the hypofluorite addition reaction to the (per)halo-olefin. After the last olefin addition the reaction product is separated from the catalyst and from the optional reaction solvent, by using known separation methods, such for example filtration, distillation or stripping under vacuum.

The yields of the addition reaction to (per)halo-olefins, also in absence of diluent, are high, generally in the range 50%-90% calculated with respect to the hypofluorite.

The semicontinuous process implies that the fluorination reaction be carried out at the above temperatures, by flowing gaseous fluorine, optionally diluted with an inert gas such as, for example, nitrogen, helium, $CF_4$, $C_2F_6$, $C_3F_8$, in the suspension containing the catalyst and the acylfluoride, until obtaining an acylfluoride conversion percentage from 1% to 80%, preferably from 5% to 60%. The fluorine conversion is complete. When the fluorine addition is over, the (per)haloolefin is added to the suspension containing the hypofluorite, the catalyst and the unreacted acylfluoride, at a temperature from 0° C. to −120° C., preferably from −60° C. to −110° C., until to a complete hypofluorite conversion. The olefin can be added as such or dispersed in a liquid or gaseous diluent, selected from those above mentioned for the addition reaction. When the olefin addition is ended, one proceeds with a further fluorination reaction with conversion of other acylfluoride to hypofluorite, followed by a second addition of olefin. The sequence of the fluorination and addition reactions is repeated until obtaining the complete acylfluoride conversion. The addition yields to the (per)haloolefins, also in absence of the inert diluent, are very high, generally in the range 50%-90% calculated with respect to the hypofluorite.

The advantage of the semicontinuous process resides in that a sole reactor is used, eliminating the hypofluorite transfer from the fluorination reactor to that in which the addition reaction takes place, which as said can give rise to decomposition phenomena. Also in absence of reaction solvent the addition yields are high.

In the continuous process two separate reactors are used. In the first reactor (reactor 1) the acylfluoride fluorination reaction takes place, in the second reactor (reactor 2) the addition to the (per)halo-olefin. In the fluorination the conversion of the reactant in defect is complete with respect to the equimolar ratio between acylfluoride equivalents and fluorine moles. The hypofluorite fluorination yield, calculated with respect to the reactant in defect, is very high, generally higher than 95%.

When in the fluorination step a) of the continuous process the reactant in defect is fluorine, the reaction is preferably carried out in absence of diluents, both liquid and gaseous; when the reactant in defect is the acylfluoride (fluorine in excess), or when the reactants are introduced in stoichiometric amounts, it is preferred to operate in the presence of an inert diluent, selected for example from those above indicated for the fluorination reaction.

The formed hypofluorite, and the optional unreacted acylfluoride are fed to the reactor 2. In the latter reactor, besides the mixture containing hypofluorite and acylfluoride, the (per)halo-olefin is introduced in a continuous way at the pure state, or diluted with a suitable inert, gaseous or liquid diluent, selected from those indicated above for the addition reaction.

In step b) of the continuous process the ratio between the equivalents of hypofluorite/hour (eq. —OF/h) and the equivalents of olefin/hour (eq. olefin/h) which are contemporaneously introduced into the addition reactor is from 0.5 to 2.0, preferably from 0.8 to 1.2.

The reaction raw product, containing the unreacted acylfluorides and the addition product, is continuously recovered from the bottom of the reactor 2 and fed to the fluorination reactor 1 wherein the still present acylfluorides are fluorinated to hypofluorites with elemental fluorine, then fed again to the addition reactor.

With the continuous process the complete acylfluoride conversion into the corresponding (per)halo-ether is obtained. It is collected as liquid in the addition reactor and optionally purified by simple distillation.

Even in absence of inert diluents, the addition yields of hypofluorites to (per)halo-olefins, calculated with respect to the hypofluorite, are very high, generally in the range 50%-90%.

In the continuous process one preferably operates in step a) with fluorine in defect, still more preferably in absence of inert diluents, with very good productivity of the (per)halo-ethers. In particular said result is obtained also by using hypofluorites having a high boiling point.

The reaction solvent absence allows to obtain the following advantages:
- to eliminate the environmental dangers connected to the solvent use;
- to recover the reaction products avoiding high distillation volumes;
- to reduce the plant operating costs.

The present invention process comprising the hypofluorite synthesis and the addition reaction with (per)halo-olefins is particularly advantageous for the hypofluorites having a boiling point higher than −10° C.

As it has been seen, in the prior art using said hypofluorites for obtaining (per)haloethers, it is difficult to avoid partial or total condensation phenomena of hypofluorites, in correspondence of which, as said, very exothermic undesired decomposition reactions can take place, reducing drastically the (per)haloethers yields.

A further object of the present invention are hypofluorites of formula (II), wherein L=1, Rf is as defined, X' has the following meanings:
F, linear or branched $C_1$-$C_3$ per(halo)alkyl; preferably perfluoroalkyl, wherein optionally one fluorine atom is substituted with one chlorine atom; or
—[O]$_T$CF$_2$CF$_2$OF,
wherein T=0 when Rf=Rf″ as above defined; T=1 when Rf=Rf′ as above.

The preferred hypofluorites are the following:
$CF_3OCF_2OCF_2CF_2OF$, $CF_3OCF_2CF_2OCF_2CF_2OF$,
$CF_3CF_2OCF_2CF_2OF$, $CF_3CF_2OCF_2CF_2OCF_2CF_2OF$,
$CF_3OCF_2OCF_2OCF_2CF_2OF$,
$CF_3OCF_2OCF_2CF_2OCF_2CF_2OF$,
$CF_3OCF_2CF_2OCF_2OCF_2CF_2OF$,
$FOCF_2CF_2OCF_2OCF_2CF_2OF$,
$FOCF_2CF_2OCF_2CF_2OCF_2CF_2OF$,
$FOCF_2CF_2OCF_2OCF_2CF_2OCF_2CF_2OF$,
$FOCF_2CF_2OCF_2OCF_2OCF_2CF_2OF$,
$FOCF_2CF_2OCF_2CF_2OCF_2CF_2OCF_2CF_2OF$.

As said, the hypofluorites of the present invention, used according to the above process, allow to obtain high yields in (per)haloether products by addition to (per)haloolefins.

This is surprising since hypofluorites having a different structure, for exampale having the carbon atom in beta position with respect to the hypofluorite oxygen substituted with a $CF_3$ group, or having the hypofluorite oxygen linked to a linear perfluoroalkyl chain with at least three carbon atoms, react with (per)halo-olefins with very low yields in the addition products (see comparative Examples). It is furthermore surprising that the present invention hypofluorites, which can also have a number of carbon atoms in the chain higher than two, are capable to react with the fluoroolefins with good yields, contrary to the teachings of the prior art.

The following Examples illustrate the invention without limiting the purpose thereof.

EXAMPLE 1

Preparation of the CsF Catalyst

The CsF catalyst, finely milled in an inert atmosphere, is fed to the reactor and dried under a gas stream inert at the temperature of 200°-250° C. for two hours. The so anhydrified catalyst is subsequently fluorinated at 400 mbar ($4 \times 10^4$ Pa) of fluorine at the temperature of 150° C. for 2 hours, then the fluorine is stripped under vacuum before being used.

EXAMPLE 2

Test in a discontinuous way according to the invention process carrying out the synthesis of the bis-hypofluorite of formula $FOCF_2CF_2O$—$(CF_2CF_2O)_m(CF_2O)_n$—$CF_2CF_2OF$ (1) by using the CsF catalyst and fluorine in excess with respect to the starting acylfluoride.

0.90 g of CsF catalyst prepared as described in Example 1 are introduced in a 10 ml metal reactor, equipped with internal thermocouple.

Then by operating under inert atmosphere (dry-box) 2 mmoles of diacylfluoride of formula $$F(O)CCF_2O—(CF_2CF_2O)_m(CF_2O)_n—CF_2C(O)F \qquad (2\text{-}A)$$

having number average MW 460 are introduced; m/n=4.50 and having a functionality in —COF end groups 1.82 and functionality in —$CF_2CF_3$ end groups 0.18, prepared as from the method described in U.S. Pat. No. 5,258,110 and U.S. Pat. No. 3,847,978.

After cooling in liquid nitrogen, and removal by stripping of the possible uncondensable products under vacuum, 5.47 mmoles of fluorine are added. The reaction mixture is brought to −10° C. and it is let react for 4 hours. It is cooled at −196° C. and 1.70 mmoles of unreacted $F_2$ are recovered and eliminated. The reaction mixture is brought to −105° C. and after having condensed 3 mmoles of perfluoropropane ($C_3F_8$), 5.47 mmoles of CFCl=CFCl are slowly added maintaining the temperature at −105° C. When the addition is over, the reaction mixture is left at −105° C. for 1 hour, then brought to the temperature of −70° C. The volatile products are removed by water pump and the reaction mixture is recovered in $C_6F_6$. The $^{19}$F-NMR and GC/MS analyses show the complete disappearance of the initial —COF end groups.

The absence of the starting acylfluorides in the final reaction mixture, besides confirming the fluorine balance obtained in the fluorination, shows that under these experimental conditions the acylfluoride conversion into the corresponding hypofluorites is quantitative.

The formed hypofluoride has the following formula:

$$FOCF_2CF_2O—(CF_2CF_2O)_m(CF_2O)_n—CF_2CF_2OF \quad (1)$$

wherein m and n are as above defined.

On the basis of the analysis, at the end of the process the formed perfluoropolyether compounds have the following end groups:
- —OCFClCF$_2$Cl, deriving from the reaction of the olefin CFCl=CFCl with the end —OF functions of the hypofluorite of formula (1), with 83% yield with respect to the moles of the initial acylfluoride;
- —OCF$_3$, deriving from the decomposition of the —CF$_2$CF$_2$OF end groups of the hypofluorite (1), with contemporaneous formation of COF$_2$. Yield of —OCF$_3$ end groups: 17%, calculated as above.

By GC/MS and GC analyses the following products have also been identified and quantified in the mixture of the reaction products (as % molar):

| | | |
|---|---|---|
| a) | ClCF$_2$CFClOCF$_2$CF$_2$O—(CF$_2$CF$_2$O)$_m$(CF$_2$O)$_n$—CF$_2$CF$_2$OCFClCF$_2$Cl | 70%; |
| b) | CF$_3$O—(CF$_2$CF$_2$O)$_m$(CF$_2$O)$_n$—CF$_2$CF$_2$OCFClCF$_2$Cl | 27%; |
| c) | CF$_3$O—(CF$_2$CF$_2$O)$_m$(CF$_2$O)$_n$—CF$_3$ | 3%. |

The reaction products are separated by fractional distillation.

Characterization:

$^{19}$F-NMR of the reaction mixture:

$^{19}$F-NMR spectrum in ppm with respect to CFCl$_3$ on the mixture (ppm=0):

−51.7, −55.3 (2F—OCF$_2$O—); −56.2 (3F C F$_3$OCF$_2$CF$_2$O—); −57.8 (3F CF$_3$OCF$_2$O—); −71.0 (2F—CF$_2$Cl); −76.5 (1F—CFCl); −87.5 (3F CF$_3$CF$_2$O—); −88.4, −90.7 (4F —OCF$_2$CF$_2$O—).

Example 2 has been summarized in Table 1.

EXAMPLES 2A-2C

Likewise Example 2, the Examples 2A and 2C have been performed and have been summarized in Table 1.

EXAMPLES 3-3B

In these Examples, which have been summarized in Table 1, the process according to the present invention is carried out starting from a diacylfluoride having a higher molecular weight, homologue of that used in Example 2 and prepared according to patents mentioned therein, having the following characteristics: molecular weight 620, m/n=4.30, functionality in —COF end groups=1.82, functionality in —CF$_2$CF$_3$ end groups=0.18.

The fluorination and addition reactions of the olefin are substantially carried out as described in Example 2.

Table 1 shows that by operating in excess of fluorine, as in the Examples 2-2C and 3-3B, the conversion of diacylfluoride into bis-hypofluorite is quantitative and the olefin addition yields are high.

EXAMPLE 4

Test in a discontinuous way according to the invention process wherein the synthesis of the bis-hypofluorite (1) is carried out by partial fluorination of the corresponding diacylfluoride on CsF catalyst.

2 mmoles of diacylfluoride of formula $$F(O)CCF_2O—(CF_2CF_2O)_m(CF_2O)_n—CF_2C(O)F$$

having number average MW 620 are introduced in a 10 ml metal reactor, equipped with internal thermocouple containing the CsF catalyst (0.90 g), by operating likewise as in Example 2; m/n=4.30, functionalaity in —COF end groups 1.82, functionality in —CF$_2$CF$_3$ end groups 0.18, prepared as indicated in patents reported in Example 2.

After cooling in liquid nitrogen, the possible uncondensable products stripped, 2.50 mmoles of fluorine are added and the reaction mixture is left at −10° C. for 4 hours. At the end of the fluorination it is found that the fluorine conversion is complete.

At the temperature of −105° C., after having condensed 3 mmoles of perfluoropropane ($C_3F_8$), 3.5 mmoles of CFCl=CFCl are slowly added. When the addition is over, the reaction mixture is left at −105° C. for 1 hour, then brought to the temperature of −70° C. The volatile products are removed by water pump.

The reaction products are then recovered in $C_6F_6$. The $^{19}$F-NMR analysis shows that the conversion of the initial —COF end groups is 69%.

The amount of each type of end group formed, calculated in % by moles with respect to the converted diacylfluoride, is respectively the following:

| | |
|---|---|
| —OCFClCF$_2$Cl | 62%; |
| —OCF$_3$ | 38%. |

Example 4 is summarized in Table 1.

By the GC/MS and GC analyses it is shown that the reaction mixture is formed, besides the starting diacylfluorides, which represent 27% by moles with respect to the initial moles, also by the following reaction products, in the indicated percentages, likewise calculated:

| | | |
|---|---|---|
| a) | $ClCF_2CFClOCF_2CF_2O$—$(CF_2CF_2O)_m(CF_2O)_n$—$CF_2CF_2OCFClCF_2Cl$ | 29%; |
| b) | $CF_3O$—$(CF_2CF_2O)_m(CF_2O)_n$—$CF_2CF_2OCFClCF_2Cl$ | 23%; |
| c) | $CF_3O$—$(CF_2CF_2O)_m(CF_2O)_n$—$CF_3$ | 13%; |
| d) | $F(O)CCF_2O$—$(CF_2CF_2O)_m(CF_2O)_n$—$CF_2CF_2OCFClCF_2Cl$ | 5%; |
| e) | $F(O)CCF_2O$—$(CF_2CF_2O)_m(CF_2O)_n$—$CF_3$ | 3%. |

The reaction products a), b), c) have been obtained, similarly to the products of Example 2, by addition of the olefin CFCl=CFCl to the corresponding bis-hypofluorites of formula (1) (see Example 2); the products d) and e) derive from the addition of the olefin to the corresponding mono-hypofluorites having the following formula (2):

$$F(O)CCF_2O\text{—}(CF_2CF_2O)_m(CF_2O)_n\text{—}CF_2CF_2OF \qquad (2).$$

The quantitative gaschromatographic analysis of all said products has shown that in the partial fluorination reaction of the diacylfluorides the selectivity is the following:

| | |
|---|---|
| bis-hypofluorites (1) | 65% |
| mono-hypofluorites (2) | 8% |
| diacylfluorides | 27% |

The Example shows that under said experimental conditions the fluorination reaction of diacylfluorides in the presence of the CsF catalyst, even by operating with lower fluorine amounts (molar) with respect to the initially present —COF end groups, mainly supplies bis-hypofluorite products (1) with a quantitative conversion of the used fluorine.

The reaction products are separated by fractional distillation.

$^{19}$F-NMR spectrum in ppm with respect to $CFCl_3$ on the mixture (ppm=0):
13.2 (1F F(O)CC$\underline{F}_2$OCF$_2$O—); 13.0 (1F F(O)CCF$_2$OC$\underline{F}_2$CF$_2$O—); −51.7, −55.3 (2F —OCF$_2$O—); −56.2 (3F CF$_3$OC$\underline{F}_2$CF$_2$O—); −57.8 (3F CF$_3$OC$\underline{F}_2$O—); −71.0 (2F =C$\underline{F}_2$Cl); −76.5 (1F —C$\underline{F}$Cl); −77.0 (2F —OCF$_2$CF$_2$OC$\underline{F}_2$C(O)F); −78.8 (2F —OCF$_2$OC$\underline{F}_2$C(O)F); −87.5 (3F C$\underline{F}_3$C$\underline{F}_2$O—); −88.4, −90.7 (4F —OC$\underline{F}_2$CF$_2$O—).

EXAMPLE 4A

Test in a discontinuous way according to the invention process wherein the synthesis of the bis-hypofluorite (1) and mono-hypofluorite (2) is carried out by partial fluorination of the corresponding diacylfluoride on CsF catalyst 2 mmoles of the diacylfluoride used in Example 4 are fed in a 10 ml metal reactor equipped with internal thermocouple containing the CsF catalyst (0.90 g), by operating likewise as in Example 2.

After cooling in liquid nitrogen, the possible uncondensable products stripped, 2.0 mmoles of fluorine are added and the reaction mixture is left at −10° C. for 4 hours. At the end of the fluorination it is found that the fluorine conversion is complete. 2.80 mmoles of $CF_2$=$CF_2$ are slowly added in the same reactor, brought to the temperature of −105° C., after having condensed 3 mmoles of perfluoropropane ($C_3F_8$). When the addition is over, the reaction mixture is then left at −105° C. for 1 hour, then brought to the temperature of −70° C., the volatile products are removed by water pump.

The reaction products are then recovered in $C_6F_6$. The $^{19}$FNMR analysis shows that the conversion of the initial —COF end groups is 55%. The amount of each end group formed, calculated as % by moles with respect to the converted diacylfluoride, is respectively the following:

| | |
|---|---|
| —OCF$_2$CF$_3$ | 32% |
| —OCF$_3$ | 68% |

The GC/MS and GC analyses have shown that the following reaction products are formed: monoacylfluorides and neutral perfluoropolyethers, besides the starting unreacted diacylfluorides which represent the 39% by moles with respect to the initial ones, in the following relative molar percentages, determined by gaschromatography:

monoacylfluorides:

| | |
|---|---|
| $CF_3CF_2O$—$(CF_2CF_2O)_m(CF_2O)_n$—$CF_2C(O)F$ | 6% |
| $CF_3O$—$(CF_2CF_2O)_m(CF_2O)_n$—$CF_2C(O)F$ | 13% |
| neutral perfluoropolyethers | |
| $CF_3CF_2O$—$(CF_2CF_2O)_m(CF_2O)_n$—$CF_2CF_3$ | 10% |
| $CF_3O$—$(CF_2CF_2O)_m(CF_2O)_n$—$CF_3$ | 11% |
| $CF_3CF_2O$—$(CF_2CF_2O)_m(CF_2O)_n$—$CF_3$ | 21% |

The reaction products are separated by fractional distillation.

Characterization of the products: $^{19}$F-NMR $^{19}$F-NMR spectrum in p.p.m. with respect to $CFCl_3$ (p.p.m.=0): 13.2 (1F F(O)CC$\underline{F}_2$OCF$_2$O—); 13.0 (1F F(O)CCF$_2$OC$\underline{F}_2$CF$_2$O—); −51.7, −55.3 (2F —OCF$_2$O—); −56.2 (3F CF$_3$OC$\underline{F}_2$CF$_2$O—); −57.8 (3F CF$_3$OC$\underline{F}_2$O—); −77.0 (2F —OC$\underline{F}_2$CF$_2$OC$\underline{F}_2$C(O)F); −78.8 (2F —OCF$_2$OC$\underline{F}_2$C(O)F); −87.5 (3F C$\underline{F}_3$CF$_2$O—); −88.4, −90.7 (4F —OC$\underline{F}_2$CF$_2$O—).

The conditions used in this Example and the obtained results are summarized in Table 1A.

EXAMPLES 4B AND 4C

Test in a discontinuous way according to the invention process wherein the synthesis of the bis-hypofluorite (1) and monohypofluorite (2) is carried out by partial fluorination of the corresponding diacylfluoride on CsF catalyst Example 4B is carried out likewise as in Example 4A but by starting from diacylfluoride having number average molecular weight 460 described in Example 2.

Example 4C is carried out likewise as in Example 4 by starting from the diacylfluoride having number average molecular weight 620 but fluorinating the compound at a temperature of +20° C. for 4 hours.

The obtained results are shown in Table 1A.

EXAMPLE 5

Test in a discontinuous way according to the invention process wherein in the fluorination a mixture of bis-hypofluorite (1) and mono-hypofluorite F(O)CCF$_2$O—(CF$_2$CF$_2$O)$_m$(CF$_2$O)$_n$—CF$_2$CF$_2$OF (2) is obtained by partial fluorination of the corresponding diacylfluoride on KHF$_2$ catalyst 3.4 g of KHF$_2$ catalyst (43 mmoles; Aldrich® Chemical Co.) are introduced in a 10 ml metal reactor, equipped with internal thermocouple and subsequently fluorinated at 400 mbar of fluorine at room temperature for 2 hours.

After fluorine removal by stripping at –196° C., by operating under inert atmosphere (dry-box), 1.90 mmoles of diacylfluoride (2-A) are introduced, as in Example 2.

After cooling in liquid nitrogen, the possible uncondensable products stripped, 2.80 mmoles of fluorine are added and the reaction mixture is left at –10° C. for 5 hours. At the end of the fluorination it is noticed that the fluorine conversion is complete. At the temperature of –105° C., after having condensed 3 mmoles of perfluoropropane (C$_3$F$_8$), 3.15 mmoles of CFCl=CFCl are slowly added.

The reaction mixture is then at –105° C. for 1 hour and subsequently brought to the temperature of –70° C. The volatile products are removed by water pump.

The reaction mixture is then recovered in C$_6$F$_6$. The $^{19}$F-NMR analysis shows that the conversion of the initial —COF end groups is 80%.

The amount of each type of end group formed, calculated in % by moles with respect to the converted diacylfluoride, is respectively the following:

| | |
|---|---|
| —OCFClCF$_2$Cl | 73%; |
| —OCF$_3$ | 27%. |

By the GC/MS and GC analyses it is shown that the reaction mixture is formed, besides by the starting diacylfluorides, which represent 4% by moles with respect to the initial moles, also by the following reaction products, in the indicated percentages, likewise calculated:

| | | |
|---|---|---|
| a) | ClCF$_2$CFClOCF$_2$CF$_2$O—(CF$_2$CF$_2$O)$_m$(CF$_2$O)$_n$—CF$_2$CF$_2$OCFClCF$_2$Cl | 38%; |
| b) | CF$_3$O—(CF$_2$CF$_2$O)$_m$(CF$_2$O)$_n$—CF$_2$CF$_2$OCFClCF$_2$Cl | 14%; |
| c) | CF$_3$O—(CF$_2$CF$_2$O)$_m$(CF$_2$O)$_n$—CF$_3$ | 12%; |
| d) | F(O)CCF$_2$O—(CF$_2$CF$_2$O)$_m$(CF$_2$O)$_n$—CF$_2$CF$_2$OCFClCF$_2$Cl | 26%; |
| e) | F(O)CCF$_2$O—(CF$_2$CF$_2$O)$_m$(CF$_2$O)$_n$—CF$_3$ | 6%. |

The reaction products a), b), c) have been obtained, similarly to the products of Example 2, by addition of the olefin CFCl=CFCl to the corresponding bis-hypofluorites (1); the products d) and e) derive from the addition of the olefin to the corresponding mono-hypofluorites (2) (Example 4).

The quantitative gaschromatographic analysis of all said products has shown that in the fluorination reaction, by using the KHF$_2$ catalyst, the selectivity for each product which is in the reacted mixture is the following:

| | |
|---|---|
| bis-hypofluorites (1) | 64% |
| mono-hypofluorites (2) | 32% |
| diacylfluorides | 4% |

In particular for the addition reaction of the olefin CFCl=CFCl to the mono-hypofluorites (2), it has been found that the yield in —OCFClCF$_2$Cl end groups is 81%, and the yield in —OCF$_3$ end groups is 19%, calculated on the moles of the formed monohypofluorites.

The reaction products are separated by fractional distillation.

$^{19}$F-NMR spectrum in ppm with respect to CFCl$_3$ of the mixture (ppm=0):
13.2 (1F F(O)CCF$_2$OCF$_2$O—); 13.0 (1F F(O)CCF$_2$OCF$_2$CF$_2$O—); –51.7, –55.3 (2F —OCF$_2$O—); –56.2 (3F CF$_3$OCF$_2$CF$_2$O—); –57.8 (3F CF$_3$OCF$_2$O—); –71.0 (2F =CF$_2$Cl); –76.5 (1F —CFCl); –77.0 (2F —OCF$_2$CF$_2$OCF$_2$C(O)F); –78.8 (2F —OCF$_2$OCF$_2$C(O)F); –87.5 (3F CF$_3$CF$_2$O—); –88.4, –90.7 (4F —OCF$_2$CF$_2$O—).

Example 5 is summarized in Table 2.

EXAMPLE 6

Example 6 has been carried out as Example 5 but by using in the fluorination reaction a diacylfluoride similar to that used in Examples 3-3B, having molecular weight 620, m/n=4.30, functionality in —COF end groups=1.82, functionality in —CF$_2$CF$_3$ end groups=0.18

The Example has been summarized in Table 2.

Table 2 shows that the fluorine conversion under the used experimental conditions is substantially quantitative independently from the molecular weight of the diacylfluoride. The addition yields of monohypofluorites (2), similarly to those of the bis-hypofluorites (1), are very high.

EXAMPLE 7

Test in a semi-continuous way according to the invention process with synthesis of the bis-hypofluorite (1) carried out by fluorination in fluorine excess of the corresponding diacylfluoride on CsF catalyst 0.90 g of CsF catalyst are introduced in a 10 ml metal reactor, equipped with internal thermocouple and subsequently activated as per Example 1.

After fluorine removal by operating under inert atmosphere (dry-box) 2 mmoles of diacylfluoride used in the Examples 3-3B are introduced. After cooling in liquid nitrogen, the possible uncondensable products stripped under vacuum, 1.83 mmoles of fluorine are added. After the reaction mixture has been brought to –10° C., it is let react for 2 hours obtaining the complete disappearance of the fed fluorine. The reaction mixture is brought to –105° C. and after having condensed 3 mmoles of perfluoropropane (C$_3$F$_8$), 1.0 mmoles of CFCl=CFCl are slowly added, maintainaing the temperature at –105° C.

When the addition is over, the reaction mixture is left at –105° C. for 1 hour and then the fluorination and olefin addition reactions are repeated as described hereinafter.

The reaction mixture is brought to the temperature of –196° C., 3.67 mmoles of fluorine are added, the temperature is increased to –10° C. maintaining the reaction mixture under said conditions for 2 hours. It is cooled again to –196° C. and 0.67 mmoles of unreacted F$_2$ are recovered, which is removed by stripping. The temperature is brought to –105° C. and 5.47 mmoles of CFCl=CFCl are slowly added.

The temperature is maintained at –105° C. for 1 hour and then it is increased to –70° C., removing the volatile products by water pump.

The reaction mixture is then recovered in C$_6$F$_6$ and analyzed by $^{19}$F-NMR analysis. The diacylfluoride conversion is 90%.

The amount of each type of end group formed, calculated in % by moles with respect to the converted diacylfluoride, is respectively the following:
—OCFClCF$_2$Cl: 62%;
—OCF$_{3—:38}$%.

The main reaction products of the addition of the olefin CFCl=CFCl to the bis-hypofluorite (1) have been identified and quantified by GC/MS and GC analyses.

Said products are equal, respectively, to the products a), b) and c) obtained in Example 2. The selectivity is comparable to that obtained in Example 2.

The reaction products are separated by fractional distillation.

The product characterization by $^{19}$F-NMR is equal to that reported in Example 2.

EXAMPLE 8

Comparative

Synthesis of the Perfluoroalkyl Hypofluorite CF$_3$CF$_2$CF$_2$OF and Addition to the Olefin CFCl=CFCl 0.90 g of CsF catalyst, prepared as described in Example 1, are introduced in a 10 ml metal reactor, equipped with internal thermocouple, and 2 mmoles of CF$_3$CF$_2$C(O)F, obtained as in Example 7 of U.S. Pat. No. 4,769,184, and 4 mmoles of fluorine are condensed on the catalyst. It is let react at –80° C. for 3 hours. After cooling in liquid nitrogen, 2 mmoles of unreacted fluorine are recovered, obtaining an acylfluoride conversion of 100%.

After removal of the fluorine in excess by stripping, the obtained hypofluorite CF$_3$CF$_2$CF$_2$OF is slowly added, at the temperature of –105° C., in a 25 ml glass reactor, equipped with magnetic stirrer and internal thermocouple, wherein 6 mmoles of CFCl=CFCl and 12 mmoles of CFCl$_3$ were previously condensed. When the addition is over, the reaction mixture is left at –105° C. for 1 hour. The $^{19}$F-NMR and GC/MS analyses on the reaction mixture have shown the complete disappearance of the initial acylfluoride CF$_3$CF$_2$C(O)F to mainly give the COF$_2$, CF$_3$CF$_3$ degradation products and, in a small part, with a yield by moles of 4% with respect to the initial acylfluoride, the addition product to the olefin having formula CF$_3$CF$_2$CF$_2$OCFClCF$_2$Cl.

This example shows that hypofluorites having a linear sequence of carbon atoms equal to or higher than 3 sum the olefins with very low yields.

EXAMPLE 9

Comparative

Synthesis of the Hypofluorite CF$_3$O(CF$_3$)CFCF$_2$OF (Beta-Branched Oxyalkylene Hypofluorite) and Addition to the Olefin CFCl=CFCl (Comparative Test)

0.90 g of CsF catalyst, prepared as in Example 1, are introduced in a 10 ml metal reactor, equipped with internal thermocouple, and 2 mmoles of the acylfluoride of formula CF$_3$O(CF$_3$)CFC(O)F, obtained as in Example IV of U.S. Pat. No. 3,114,778, and 4 mmoles of fluorine are condensed on the catalyst. It is let react at –80° C. for 4 hours. After cooling in liquid nitrogen, 1.6 mmoles of unreacted fluorine are recovered. After removal of the fluorine in excess by stripping, the obtained hypofluorite CF$_3$O(CF$_3$)CFCF$_2$OF is slowly added, at the temperature of –80° C., in a 25 cc glass reactor, equipped with magnetic stirrer and internal thermocouple, wherein 6 mmoles of CFCl=CFCl and 12 mmoles of CFCl$_3$ were previously condensed.

When the addition is over, the reaction mixture is left at –80° C. for 1 hour. The $^{19}$F-NMR and GC/MS analyses on the reaction mixture have shown a conversion of 93% of the initial acylfluoride CF$_3$O(CF$_3$)CFC(O)F to give the COF$_2$, CF$_3$OCF$_2$CF$_3$, CF$_3$OCFClCF$_2$Cl products deriving from the hypofluorite degradation and, in a small part, with a yield of 2% with respect to the initial acylfluoride, the addition product of the hypofluorite to the olefin having formula CF$_3$O(CF$_3$)CFCF$_2$OCFClCF$_2$Cl.

EXAMPLE 10

Test in a discontinuous way according to the invention process carrying out the synthesis of the bis-hypofluorite of formula FOCF$_2$CF$_2$O—(CF$_2$CF$_2$O)$_m$(CF$_2$O)$_n$—CF$_2$CF$_2$OF (1) by using the CsF catalyst and fluorine in excess with respect to the starting acylfluoride 0.90 g of CsF catalyst prepared as described in Example 1 are introduced in a 10 ml metal reactor equipped with internal thermocouple.

By working likewise as in Example 2 mmoles of diacylfluoride F(O)CCF$_2$O—(CF$_2$CF$_2$O)$_m$(CF$_2$O)$_n$—CF$_2$C(O)F having average molecular weight (MW) 620 are introduced; m/n 4.30, functionality in —COF end groups 1.82, functionality in —CF$_2$CF$_3$ end groups 0.18, used in Examples 3-3B.

After cooling in liquid nitrogen, the possible uncondensable products stripped under vacuum, 5.47 mmoles of fluorine are added and the reaction mixture is left at –10° C. for 4 hours. It is cooled to –196° C. and 1.70 mmoles of unreacted F$_2$, which is removed, are recovered. The reaction mixture is brought to –105° C., and 3 mmoles of perfluoropropane (C$_3$F$_8$) are condensed. The reaction mixture is then brought at the temperature of –55° C. and 4.37 mmoles of trans-1,2-dichloroethylene CHCl=CHCl are slowly added. When the addition is over the reaction is left at –55° C. for 1 hour. The volatile products are removed by water pump and the reaction mixture is recovered in C$_6$F$_6$. The $^{19}$F-NMR analyses show the complete disappearance of the initial —COF end groups.

The amount of each end group formed, expressed in % by moles with respect to the converted diacylfluoride, is respectively the following:

| | |
|---|---|
| —OCHClCHFCl | 41% |
| —OCF$_3$ | 59% |

By GC/MS and GC analyses the following products have been identified and quantified in the reaction mixture (% relative molar):

| | |
|---|---|
| ClFHCCHClOCF$_2$CF$_2$O—(CF$_2$CF$_2$O)$_m$(CF$_2$O)$_n$—CF$_2$CF$_2$OCHClCHFCl | 24% |
| CF$_3$O—(CF$_2$CF$_2$O)$_m$(CF$_2$O)$_n$—CF$_2$CF$_2$OCHClCHFCl | 35% |
| CF$_3$O—(CF$_2$CF$_2$O)$_m$(CF$_2$O)$_n$—CF$_3$ | 41% |

The products are separated by fractional distillation.

$^{19}$F-NMR spectrum in p.p.m. with respect to CFCl$_3$ (p.p.m.=0): −51.7, −55.3 (2F —OCF$_2$O—); −56.2 (3F CF$_3$OCF$_2$CF$_2$O—); −57.8 (3F CF$_3$OCF$_2$O—); −87.5 (3F CF$_3$CF$_2$O—); −88.4, −90.7 (4F —OCF$_2$CF$_2$O—); −91.1, −91.8 (2F —OCF$_2$CF$_2$OCHClCHFCl); −143.4, −145.2 (1F —OCF$_2$CF$_2$OCHClCHFCl).

EXAMPLES 10A-10E

These Examples have been carried out likewise as in Example 10, except for the following differences:

In Example 10D the ethyl acrylate olefin (4.37 mmoles) has been added in the reactor at the temperature of −196° C. and the reaction mixture has been let reach the temperature of −50° C., then left at this temperature for one hour.

In Example 10E the maleic anhydride olefin (4.37 mmoles) dissolved in acetonitrile (2 ml) has been added in the reactor at the temperature of −196° C. and the reaction mixture has been let reach the temperature of −30° C. and left at this temperature for one hour.

The obtained results have been summarized in Table 3.

EXAMPLE 11

Test in a discontinuous way according to the invention process wherein the synthesis of the bis-hypofluorite (1) and mono-hypofluorite (2) is carried out by partial fluorination of the corresponding diacylfluoride on CsF catalyst and addition to CHCl=CHCl 2 mmoles of diacylfluoride F(O)CCF$_2$O—(CF$_2$CF$_2$O)$_m$(CF$_2$O)$_n$—CF$_2$C(O)F used in Examples 4 and 3-3B, are introduced in a 10 ml metal reactor equipped with internal thermocouple and containing the CsF catalyst (0.90 g), by operating likewise as in Example 4.

After cooling in liquid nitrogen, the possible uncondensable products stripped, 2.10 mmoles of fluorine are added and the reaction mixture is left at −10° C. for 4 hours. At the end of the fluorination it is found that the fluorine conversion is complete. At the temperature of −80° C., after having condensed in the reactor 3 mmoles of A-11 (CFCl$_3$), 2.80 mmoles of trans 1-2 dichloroethylene are slowly added. When the addition is over, the reaction mixture is then left at −80° C. for one h, then brought to −50° C., and the volatile products are removed by water pump.

The reaction products are then recovered in C$_6$F$_6$. The $^{19}$F-NMR analysis shows that the conversion of the initial —COF end groups is 57%. The amount of each end group formed, expressed in % by moles with respect to the converted diacylfluoride, is respectively the following:

| —OCHClCHFCl | 51% |
|---|---|
| —OCF$_3$ | 49% |

By GC/MS and GC analyses it is found that the reaction mixture is formed, besides the starting diacylfluorides representing the 31% by moles with respect to the initial moles, also by the following reaction products (% relative molar):

| | |
|---|---|
| ClFHCCHClOCF$_2$CF$_2$O—(CF$_2$CF$_2$O)$_m$(CF$_2$O)$_n$—CF$_2$CF$_2$OCHClCHFCl | 12% |
| CF$_3$O—(CF$_2$CF$_2$O)$_m$(CF$_2$O)$_n$—CF$_2$CF$_2$OCHClCHFCl | 22% |
| CF$_3$O—(CF$_2$CF$_2$O)$_m$(CF$_2$O)$_n$—CF$_3$ | 11% |
| F(O)CCF$_2$O—(CF$_2$CF$_2$O)$_m$(CF$_2$O)$_n$—CF$_2$CF$_2$OCHClCHFCl | 12% |
| F(O)CCF$_2$O—(CF$_2$CF$_2$O)$_m$(CF$_2$O)$_n$—CF$_3$ | 12% |

The products are separated by fractional distillation.

$^{19}$F-NMR spectrum in p.p.m. with respect to CFCl$_3$ (p.p.m.=0): 13.2 (1F F(O)CCF$_2$OCF$_2$O—); 13.0 (1F F(O)CCF$_2$OCF$_2$CF$_2$O—); −51.7, −55.3 (2F —OCF$_2$O—); −56.2 (3F CF$_3$OCF$_2$CF$_2$O—); −57.8 (3F CF$_3$OCF$_2$O); 77.0 (2F —OCF$_2$CF$_2$OCF$_2$C(O)F); −78.8 (2F —OCF$_2$OCF$_2$C(O)F); −87.5 (3F CF$_3$CF$_2$O—); −88.4, −90.7 (4F —OCF$_2$CF$_2$O—); −91.1, −91.8 (2F —OCF$_2$CF$_2$OCHClCHFCl); −143.4, −145.2 (1F —OCF$_2$CF$_2$OCHClCHFCl).

EXAMPLE 12

Test in a discontinuous way according to the invention process wherein the synthesis of the bis-hypofluorite (1) and mono-hypofluorite (2) is carried out by partial fluorination of the corresponding diacylfluoride on CsF catalyst and addition to CF$_3$OCF=CF$_2$ 2 mmoles of diacylfluoride F(O)CCF$_2$O—(CF$_2$CF$_2$O)$_m$(CF$_2$O)$_n$—CF$_2$C(O)F of Example 4 are introduced in a 10 ml metal reactor equipped with internal thermocouple containing the CsF catalyst (0.90 g), by operating likewise as in Example 11.

After cooling in liquid nitrogen, the possible uncondensable products stripped, 1.82 mmoles of fluorine are added and the reaction mixture is left at −10° C. for 4 hours. At the end of the fluorination it is found that the fluorine conversion is complete. The reaction mixture is brought to −105° C. and after having condensed 3 mmoles of perfluoropropane (C$_3$F$_8$), 2.80 mmoles of CF$_3$OCF=CF$_2$ are added.

When the addition is over, the reaction mixture is then left at −105° C. for one h, then brought to −70° C., and the volatile products are removed by water pump.

The reaction products are then recovered in C$_6$F$_6$.

The $^{19}$F-NMR analysis shows that the conversion of the initial —COF end groups is 49% to give products having the following neutral end groups in the molar percentages indicated below, calculated with respect to the converted —COF:

| —OCF$_2$CF$_2$OCF$_3$ | 90% |
|---|---|
| —OCF(CF$_3$)OCF$_3$ | 10% |

The products are separated by fractional distillation.

$^{19}$F-NMR spectrum in p.p.m. with respect to CFCl$_3$ (p.p.m.=0): 13.2 (1F F(O)CCF$_2$OCF$_2$O—); 13.0 (1F F(O)CCF$_2$OCF$_2$CF$_2$O—); −51.7, −55.3 (2F —OCF$_2$O—); −55.4 (3F —OCF(CF$_3$)OCF$_3$); −56.2 (3F CF$_3$OCF$_2$CF$_2$O—); −57.8 (3F CF$_3$OCF$_2$O—); −77.0 (2F —OCF$_2$CF$_2$O—CF$_2$C(O)F); −78.8 (2F —OCF$_2$C(O)F); −86.7 (3F —OCF(CF$_3$)OCF$_3$); −87.5 (3F CF$_3$CF$_2$O—); −88.4, −90.7 (4F —OCF$_2$CF$_2$O—); −98.2 (1F —OCF(CF$_3$)OCF$_3$).

EXAMPLE 13

Test in a semicontinuous way according to the invention process wherein the synthesis of the bis-hypofluorite (1) is carried out by fluorination of the corresponding diacylfluoride on CsF catalyst and addition to CFCl=CFCl 2.3 g of CsF catalyst, which is activated by heating at 200° C. for 4 hours in inert atmosphere and then subsequently fluorinated with 1 Nl/h of $F_2$ diluted with 1 Nl/h of He at the temperature of 150° C. for 4 hours, are introduced in a 420 ml metal reactor equipped with reflux condenser, mechanical stirrer and internal thermocouple.

After removal of the residual fluorine, 100 g (0.22 moles) of the diacylfluoride (MW=460) of Example 2 are fed, then the reaction mixture is brought to –80° C. by an external cryostat. A mixture formed by 1.0 litres/h (l/h) of elementary fluorine diluted with 0.5 litres/h of helium is fluxed into the reator for 1 hour. The gaschromatographic analyses of the gases outflowing from the reactor show how the fluorine yield with respect to the fed fluorine is 95%.

Then the reaction mixture is brought to –105° C. by an external liquid nitrogen cryogenic system and a mixture formed by 1 Nl/h of CFCl=CFCl diluted with 4 Nl/h of He is added at the temperature of –105° C. in one hour.

The reaction mixture is brought again to –80° C. where one proceeds to a further fluorination and subsequently to a further addition of olefin, under the same above mentioned conditions. The reaction is followed by $^{19}$F-NMR analysis up to the complete conversion of the initial —COF end groups. With the sequence of the described operations a total fluorine amount of 0.42 moles is introduced with a fluorine yield of 95%.

When the rection is over, the formed products, separated from the catalyst, are analyzed by $^{19}$F-NMR analysis.

The conversion of the starting acylfluoride is quantitative.

The amount of each end group formed, expressed in % by moles with respect to the converted diacylfluoride, is respectively the following:

| | |
|---|---|
| —OCFClCF$_2$Cl | 85% |
| —OCF$_3$ | 15% |

By GC/MS and GC analysis it is shown that the reaction mixture is formed by the following reaction products in the indicated molar percentages:

| | | |
|---|---|---|
| a) | ClCF$_2$CFClOCF$_2$CF$_2$O—(CF$_2$CF$_2$O)$_m$(CF$_2$O)$_n$—CF$_2$CF$_2$OCFClCF$_2$Cl | 72% |
| b) | CF$_3$O—(CF$_2$CF$_2$O)$_m$(CF$_2$O)$_n$—CF$_2$CF$_2$OCFClCF$_2$Cl | 26% |
| c) | CF$_3$O—(CF$_2$CF$_2$O)$_m$(CF$_2$O)$_n$—CF$_3$ | 2% |

The products are separated by fractional distillation. Characterization of the products: $^{19}$F-NMR $^{19}$F-NMR spectrum in p.p.m. with respect to CFCl$_3$ (p.p.m.=0): –51.7, –55.3 (2F —OCF$_2$O—); –56.2 (3F CF$_3$OCF$_2$CF$_2$O—); –57.8 (3F CF$_0$OCF$_2$O—); –71.0 (2F —CF$_2$Cl); –76.5 (1F —CFCl); –87.5 (3F CF$_3$CF$_2$O—); –88.4, –90.7 (4F —OCF$_2$CF$_2$O—).

EXAMPLE 14

Comparative

Synthesis of the Perfluoroalkyl Hypofluorite CF$_3$CF$_2$CF$_2$OF and Subsequent Addition of the CFCl=CFCl Olefin 4.0 mmoles of CF$_3$CF$_2$C(O)F used in Example 8 are introduced in a 10 ml metal reactor equipped with internal thermocouple containing the CsF catalyst (0.90 g), operating likewise as in Example 2, and subsequently 2.0 mmoles of fluorine are added and the reaction mixture is left at –80° C. for 4 hours. At the end of the fluorination it is found that the fluorine conversion is complete. At the temperature of –105° C., after having condensed in the reactor 3 mmoles of perfluoropropane (C$_3$F$_8$), 2.80 mmoles of CFCl=CFCl are slowly added. When the addition is over, the reaction mixture is left at –105° C. for 1 hour.

The reaction products are then recovered in C$_6$F$_6$. By analyzing the reaction mixture by $^{19}$F-NMR and GC/MS analyses it has been verified that the conversion of the initial —COF end groups is of 50%. The formed products are the degradation products of the hypofluorite CF$_3$CF$_2$CF$_2$OF: COF$_2$, CF$_3$CF$_3$ and only in traces the product of addition to the the olefin CF$_3$CF$_2$CF$_2$OCFClCF$_2$Cl (molar yield<1% with respect to the converted acylfluoride).

This Example shows that the addition of olefins to hypfluorites having a linear sequence of carbon atoms equal to or higher than 3 occurs with extremely low yields.

EXAMPLE 15

Comparative

Synthesis of the Hypofluorite CF$_3$O(CF$_3$)CFCF$_2$OF and Subsequent Addition of the CFCl=CFCl Olefin 4.0 mmoles of the acylfluoride CF$_3$O(CF$_3$)CFC(O)F used in Example 9 are introduced in a 10 ml metal reactor equipped with internal thermocouple, and containing the CsF catalyst (0.90 g), operating likewise as in Example 2, and subsequently 2.0 mmoles of fluorine are added. The reaction mixture is left at –80° C. for 4 hours. At the end of the fluorination it is found that the fluorine conversion is complete. At the temperature of –105° C., after having condensed in the reactor 3 mmoles of perfluoropropane (C$_3$F$_8$), 2.80 mmoles of CFCl=CFCl are slowly added. When the addition is over, the reaction mixture is left at –105° C. for 1 hour.

The $^{19}$F-NMR and GC/MS analyses on the reaction mixture have shown a conversion of 50% of the initial acylfluoride CF$_3$O(CF$_3$)CFC(O)F to give the products COF$_2$, CF$_3$OCF$_2$CF$_3$ and CF$_3$OCFClCF$_2$Cl deriving from the degradation of the hypofluorite CF$_3$O(CF$_3$)CFCF$_2$OF and only in traces the addition product to the olefin $CF_3O(CF_3)CFCF_2OCFClCF_2Cl$ (yield about 1% with respect to the converted acylfluoride).

This Example shows that the addition of olefins to hypolfuorites having a structure similar to the product $CF_3O(CF_3)CFCF_2OF$ occurs with extremely low yields.

TABLE 1

Examples 2-2C, 3-3B and 4: conditions of diacylfluoride fluorination (in the Table the initial —COF end group mmoles), of olefin addition to the hypofluorite, % conversion —COF and % by moles of the end groups $ClCF_2CFClO$—, $CF_3CF_2O$—, $CF_3O$— formed in the reaction products; in Example 4 the % are calculated with respect to the amount of converted acylfluoride. The fluorination reaction time is 4 hours and the used catalyst is CsF (0.90 g).

| | Fluorination | | | | | | —COF | Reaction products end groups | | |
|---|---|---|---|---|---|---|---|---|---|---|
| | Reactants (amount by mmoles) | | | T° | Olefin addition | | conver. | $ClCF_2CFClO$— | $CF_3CF_2O$— | $CF_3O$— |
| Ex. | —COF | $F_2$ | $F_2$/—COF | C. | solv. | olefin | T° C. | % moles | % by moles | |
| 2 | 3.64 | 5.5 | 1.51 | −10 | $C_3F_8$ | CFCl=CFCl | −105 | 100 | 83 | — | 17 |
| 2A | 3.64 | 5.5 | 1.51 | −80 | $C_3F_8$ | CFCl=CFCl | −80 | 100 | 55 | — | 45 |
| 2B | 3.64 | 5.5 | 1.51 | −10 | $C_3F_8$ | $CF_2$=$CF_2$ | −105 | 100 | — | 48 | 52 |
| 2C | 3.0 | 6.6 | 2.20 | −80 | HT-55 | CFCl=CFCl | −80 | 100 | 80 | — | 20 |
| 3 | 3.64 | 5.5 | 1.51 | −10 | $C_3F_8$ | CFCl=CFCl | −105 | 100 | 56 | — | 44 |
| 3A | 1.85 | 4.7 | 2.54 | −80 | $C_3F_8$ | CFCl=CFCl | −80 | 100 | 39 | — | 61 |
| 3B | 3.64 | 5.5 | 1.51 | −10 | $C_3F_8$ | $CF_2$=$CF_2$ | −105 | 100 | — | 31 | 69 |
| 4 | 3.64 | 2.5 | 0.69 | −10 | $C_3F_8$ | CFCl=CFCl | −105 | 69 | 62 | — | 38 |

TABLE 1A

Examples 4A-4C: reactions in a discontinuous way
Conditions of diacylfluoride fluorination (in the Table the mmoles of initial —COF end groups, of addition of the olefin to the hypofluorite, —COF conversion % and % by moles of the end groups $ClCF_2CFClO$—, $CF_3CF_2O$—, $CF_3O$— formed in the reaction products; the % are calculated with respect to the amount of converted acylfluoride. The time of the fluorination reaction is 4 hours and the used catalyst is CsF (0.90 g).

| | Fluorination | | | | | | —COF | End groups of the reaction products | | |
|---|---|---|---|---|---|---|---|---|---|---|
| | Reactants (amounts by mmoles) | | | | Olefin addition | | convers. | $ClCF_2CFClO$— | $CF_3CF_2O$— | $CF_2O$— |
| Ex. | —COF | $F_2$ | $F_2$/—COF | T° C. | solv. | olefin | T° C. | % moles | % by moles | |
| 4A | 3.64 | 2.0 | 0.55 | −10 | $C_3F_8$ | $CF_2$=$CF_2$ | −105 | 55 | — | 32 | 68 |
| 4B | 3.64 | 2.0 | 0.55 | −10 | $C_3F_8$ | $CF_2$=$CF_2$ | −105 | 54 | — | 53 | 47 |
| 4C | 3.64 | 1.92 | 0.53 | +20 | $C_3F_8$ | CFCl=CFCl | −105 | 52 | 45 | — | 55 |

TABLE 2

Examples 5 and 6: conditions of diacylfluoride fluorination (abbrev. DACF in the Table), % conversion diacylfluoride and % molar ratio of the end groups $ClCF_2CFClO$—/$CF_3O$— formed in the reaction products, calculated with respect to the moles of converted monohypofluorite (2). The fluorination reaction temperature is −10° C. and the used catalyst $KHF_2$. In the addition reaction the temperature is −105° C., the used olefin is CFCl=CFCl and the reaction solvent $C_3F_8$.

| Diacylfluoride | | | | | Fluorination | Calculation yields of the compounds obtained in the fluorination hypofluorites | | | Molar ratio end groups —$OCFClCF_2Cl$/$OCF_3$ calculated with respect to converted mono-hypofluorite (2) |
|---|---|---|---|---|---|---|---|---|---|
| MW | End* —COF mmoles | $F_2$ mmoles | $F_2$/—COF | time hours | Conv. —COF % moles | mono- (2) % moles | bis- (1) % moles | DACF % moles | |
| 460 Ex. 5 | 3.46 | 2.80 | 0.80 | 5 | 80 | 32 | 64 | 4 | 81/19 |
| 620 Ex. 6 | 3.64 | 2.10 | 0.58 | 4 | 46 | 57 | 26 | 17 | 80/20 |

*abbreviation for: end groups

TABLE 3

Examples 10, 10A-10E, 11-12: batch reactions
Conditions of diacylfluoride fluorination (in the Table the mmoles of initial —COF end groups), of the olefin addition to the hypofluorite, —COF conversion %, formula of the reaction products end groups, % by moles of said end groups and of $CF_3O$— in the reaction products; the % are calculated with respect to the amount of converted acylfluoride. The fluorination reaction has been carried out at -10° C. in 4 hours and the used catalyst is CsF (0.90 g). In the column T° C. (1a) and (1b) the T intervals are indicated in the respective Examples.

| | Fluorination Reactants | | | | | | —COF | End groups of the reaction products | | $CF_3O$— |
|---|---|---|---|---|---|---|---|---|---|---|
| | (amount by mmoles) | | | | Olefin addition | | conver. | | | |
| Ex. | —COF | $F_2$ | $F_2$/—COF | solv. | olefin | T° C. | % moles | Formula | % moles | % moles |
| 10 | 3.64 | 5.5 | 1.51 | $C_3F_8$ | CHCl=CHCl | -55 | 100 | —OCHClCHFCl | 41 | 59 |
| 10A | 3.64 | 5.5 | 1.51 | $C_3F_8$ | $CF_3CF=CF_2$ | -80 | 100 | —$OCF_2CF_2CF_3$ | 39 | 37 |
| | | | | | | | | —$OCF(CF_3)_2$ | 24 | — |
| 10B | 3.64 | 5.5 | 1.51 | $C_3F_8$ | $CH_2=CF_2$ | -105 | 100 | —$OCH_2CF_3$ | 35 | 62 |
| | | | | | | | | —$OCF_2CH_2F$ | 3 | — |
| 10C | 3.64 | 5.5 | 1.51 | $CFCl_3$ | CHCl=$CCl_2$ | -80 | 100 | —$OCHClCFCl_2$ | 36 | 55 |
| | | | | | | | | —$OCCl_2CHFCl$ | 9 | — |
| 10D | 3.64 | 5.5 | 1.51 | $CFCl_3$ | $CH_2$=CHCOOEt | (1a) | 100 | —$OCH_2CHFCOOEt$ | 32 | 68 |
| 10E | 3.64 | 5.5 | 1.51 | $CFCl_3$ | maleic anhydr. | (1b) | 100 | 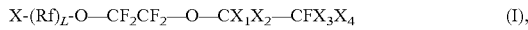 | 30 | 70 |
| 11 | 3.64 | 2.10 | 0.58 | CFCl23 | CHCl=CHCl | -80 | 57 | —OCHClCHFCl | 51 | 49 |
| 12 | 3.64 | 1.82 | 0.50 | $C_3F_6$ | $CF_2OCF=CF_2$ | -105 | 49 | —$OCF_2CF_2OCF_3$ | 90 | — |
| | | | | | | | | —$OCF(CF_3)OCF_3$ | 10 | — |

The invention claimed is:

1. (Per)haloethers having formula (I)

X-(Rf)$_L$-O—$CF_2CF_2$—O—$CX_1X_2$—$CFX_3X_4$ (I), wherein $X_1, X_2, X_3, X_4$ have the following meanings:

1) $X_1$ and $X_2$ are, independently each from the other, F, H or Cl, and $X_3$ and $X_4$ are independently each from the other, F, H, Cl or Br, wherein at least one of $X_1$ or $X_2$ is H or Cl, and at least one of $X_3$ or $X_4$ is H, Cl, or Br;

2) one of $X_1$ or $X_2$, and/or one of $X_3$ or $X_4$, is/are chosen from the following groups: —$COOR^1_H$, wherein $R^1_H$ is $C_1$-$C_3$ alkyl; —OC(O)$CH_3$; —CN; —NCO; —NCS; aryl, substituted with —$NO_2$ or non substituted; —NH—C(O)—$NH_2$; —$OC(O)_2CH_3$, —P(O)$(C_6H_5)_2$, —$P(O)_2(C_6H_5)_2$, or —$SO_2F$;

whereas the remaining substituents of the group of $X_1$, $X_2$, $X_3$, and $X_4$, have the following meanings:
$X_3$=F, $X_4$=Cl, $X_1$=F, and $X_2$=Cl;
$X_3$=F, $X_4$=Cl, $X_1$=F, and $X_2$=H;
$X_1$=$X_3$=H, and $X_2$=$X_4$=Cl; or
$X_1$=$X_3$=$X_4$=Cl, and $X_2$==H;

3) one of $X_1$ or $X_2$, and/or one of $X_3$ or $X_4$, is/are chosen from the following groups:

3a) $C_1$-$C_{20}$ linear or branched per(halo) fluorinated alkyl;

3b) $C_1$-$C_{20}$ linear or branched per(halo)fluorinated oxyalkyl; wherein when the alkyl is per(halo), there are one or more atoms of Cl and/or Br;

3c) $C_1$-$C_{10}$ linear or branched alkyl, optionally containing one or more functional groups, chosen between $COOR^1_H$, wherein $R^1_H$ is $C_1$-$C_3$ alkyl; —OC(O)$CH_3$; —CN; —NCO; —NCS; aryl, substituted with —$NO_2$ or non substituted; —NH—C(O)—$NH_2$; —OC(O)$_2$ $CH_3$, —P(O)$(C_6H_5)_2$, —$P(O)_2(C_6H_5)_2$, —$SO_2F$, and hydrogenated organic anhydrides chosen from the group of linear anhydrides of organic $C_1$-$C_4$ mono-carboxylic acids or cyclic anhydrides of $C_4$-$C_6$ dicarboxylic acids; wherein the remaining substituents of the group of $X_1$, $X_2$, $X_3$, $X_4$, independently each from the other, are F, H, Cl or Br;

4) one of $X_1$ or $X_2$, together with one of $X_3$ or $X_4$ and the two carbon atoms of the group —$CX_1X_2$—$CFX_3X_4$ form cyclic fluorinated or hydrogenated anhydride or imide compounds, containing 4-6 carbon atoms in the ring, wherein the remaining substituents between $X_1$ or $X_2$ and between $X_3$ or $X_4$, independently each from the other, are F, H, Cl or Br; and 4a) $X_3$ and $X_4$, together with the relevant carbon atom to which they are attached, form a cyclic anhydride ring having 4 carbon atoms; $X_1$ and $X_2$ independently each from the other, are F, H, Cl or Br;

X has the following meanings:
F, linear or branched $C_1$-$C_3$ per(halo)alkyl;
—[O]$_T$$CF_2CF_2OCX_1X_2$—$CFX_3X_4$, —[O]$_T$$CF_2C(O)F$,
wherein
T=0 when L=1 and Rf=Rf'' as defined below;
T=1 when L=1 and Rf=Rf' as defined below;
when L=1 and Rf=Rf' defined below, X is also $C_1$-$C_5$ perfluoroxyalkyl;
L=0, 1;
when L=0, X must not have the following meanings:
F;
[O]$_T$$CF_2CF_2OCX_1X_2$—$CFX_3X_4$ being T=0, $X_1$=F, $X_2$=Cl, $X_3$=F, $X_4$=Cl;
$C_1$-$C_3$ perfluoroalkyl when $X_3$=F and $X_4$=Cl, $X_1$=F;
when L=1, Rf=Rf' or Rf''; wherein
Rf''=$C_1$-$C_{20}$ perfluoroalkylene;
Rf'=perfluorooxyalkylene having formula:

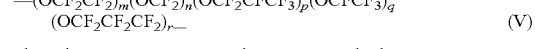

—$(OCF_2CF_2)_m(OCF_2)_n(OCF_2CFCF_3)_p(OCFCF_3)_q$ $(OCF_2CF_2CF_2)_r$— (V)

wherein m, n, p, q, r are integers such that:
m is 0 to 100;
n is 0 to 100;

p is 0 to 60;
r is 0 to 60;
q is 0 to 60; m+n+p+r+q>1; and
the average molecular weight of Rf" from 66 to 12,000.

2. (Per)haloethers according to claim 1, wherein when Rf=Rf" the perfluorooxyalkylene has the following formula:

$$—(OCF_2CF_2)_m(OCF_2)_n— \quad (VI)$$

wherein m and n independently one from the other have the above values; when both m and n are present, mm ranges from 0.1 to 6.

3. (Per)haloethers having the following formulas:

CF$_3$CF$_2$O—CF$_2$CF$_2$—O—CHCl—CFCl$_2$;
CF$_3$OCF$_2$O—CF$_2$CF$_2$—O—CFCl—CF$_2$Cl;

CF$_3$OCF$_2$CF$_2$O—CF$_2$CF$_2$—O—CFCl—CF$_2$Cl;

CF$_3$OCF$_2$OCF$_2$O—CF$_2$CF$_2$—O—CFCl—CF$_2$Cl;

CF$_3$O—CF$_2$CF$_2$—O—CHCl—CHFCl; CF$_3$O—CF$_2$CF$_2$—O—CHCl—CFCl$_2$;

CF$_3$CF$_2$O—CF$_2$CF$_2$—O—CHCl—CHFCl;

CF$_3$OCF$_2$O—CF$_2$CF$_2$—O—CHCl—CHFC$_{CF3}$OCF$_2$CF$_2$O—CF$_2$CF$_2$—O—CHCl—CHFCl;

CF$_3$OCF$_2$OCF$_2$O—CF$_2$CF$_2$—O—CHCl—CHFCl;

F(O)CCF$_2$—O—CF$_2$CF$_2$—O—CFCl—CF$_2$Cl;

F(O)CCF$_2$—O—CF$_2$CF$_2$—O—CHCl—CHFCl;

F(O)CCF$_2$—OCF$_2$O—CF$_2$CF$_2$—O—CFCl—CF$_2$Cl;

F(O)CCF$_2$—OCF$_2$O—CF$_2$CF$_2$—O—CHCl—CHFCl$_2$;

F(O)CCF$_2$—OCF$_2$O—CF$_2$CF$_2$—O—CFCl—CF$_2$Cl;

F(O)CCF$_2$—OCF$_2$OCF$_2$CF$_2$O—CF$_2$CF$_2$—O—CFCl—CF$_2$Cl;

F(O)CCF$_2$—OCF$_2$CF$_2$OCF$_2$O—CF$_2$CF$_2$—O—CFCl—CF$_2$Cl;

CHFClCHClO—CF$_2$CF$_2$—O—CF$_2$CF$_2$—O—CHCl—CHFCl;

CF$_2$ClCFClO—CF$_2$CF$_2$—OCF$_2$O—CF$_2$CF$_2$—O—CFCl—CF$_2$Cl;

CF$_2$ClCFClO—CF$_2$CF$_2$—OCF$_2$CF$_2$O—CF$_2$CF$_2$—O—CFCl—CF$_2$Cl;

CF$_2$ClCFClO—CF$_2$CF$_2$—OCF$_2$OCF$_2$CF$_2$O—CF$_2$CF$_2$—O—CFCl—CF$_2$Cl;

CFCl$_2$CHClO—CF$_2$CF$_2$—O—CF$_2$CF$_2$—O—CHCl—CFCl$_2$;

CFCl$_2$CHClO—CF$_2$CF$_2$—OCF$_2$O—CF$_2$CF$_2$—O—CHCl—CFCl$_2$;

CFCl$_2$CHClO—CF$_2$CF$_2$—OCF$_2$CF$_2$O—CF$_2$CF$_2$—O—CHCl—CFCl$_2$;

CFCl$_2$CHClO—CF$_2$CF$_2$—OCF$_2$OCF$_2$CF$_2$O—CF$_2$CF$_2$—O—CHCl—CFCl$_2$;

CF$_3$O—(CF$_2$CF$_2$O)$_m$(CF$_2$O)$_n$—CF$_2$C(O)F;

CF$_3$CF$_2$O—(CF$_2$CF$_2$O)$_m$(CF$_2$O)$_n$—CF$_2$C(O)F;

CF$_3$CF$_2$CF$_2$O—(CF$_2$CF$_2$O)$_m$(CF$_2$O)$_n$—CF$_2$C(O)F;
(CF$_3$)$_2$CFO—(CF$_2$CF$_2$O)$_m$(CF$_2$O)$_n$—CF$_2$C(O)F;

CF$_3$O—(CF$_3$)CFO—(CF$_2$CF$_2$O)$_m$(CF$_2$O)$_n$—CF$_2$C(O)F;

CF$_3$O—(CF$_2$CF$_2$O)$_m$(CF$_2$O)$_n$—CF$_2$CF$_2$OCH$_2$CF$_3$;

F(O)CCF$_2$O—(CF$_2$CF$_2$O)$_m$(CF$_2$O)$_n$—CF$_2$CF$_2$OCH$_2$CF$_3$;

F$_3$CCH$_2$OCF$_2$CF$_2$O—(CF$_2$CF$_2$O)$_m$(CF$_2$O)$_n$—CF$_2$CF$_2$OCH$_2$CF$_3$;

CF$_3$O—(CF$_2$CF$_2$O)$_m$(CF$_2$O)$_n$—CF$_2$CF$_2$OCH$_2$CHFCOOMe;

F(O)CCF$_2$O—(CF$_2$CF$_2$O)$_m$(CF$_2$O)$_n$CF$_2$—CF$_2$OCH$_2$CHFCOOMe;

MeOCOCHFCH$_2$OCF$_2$CF$_2$O—(CF$_2$CF$_2$O)$_m$(CF$_2$O)$_n$—CF$_2$CF$_2$OCH$_2$CHFCOOMe;

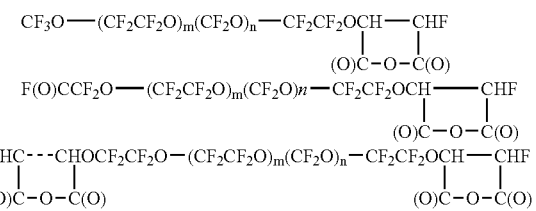

wherein: m/n =4.3 and the molecular weight of the perfluoropolyether chain —(CF$_2$CF$_2$O)$_m$(CF$_2$O)$_n$— is 620.

4. (Per)haloethers according to claim 1, wherein X$_1$, X$_2$, X$_3$, X$_4$ are selected from the group consisting of: F, H, and Cl.

5. (Per)haloethers according to claim 1, wherein X$_1$=F, X$_2$=Cl, X$_3$=F, X$_4$=Cl.

6. (Per)haloethers according to claim 1, wherein X$_1$=F, X$_2$=H, X$_3$=F, and X$_4$=Cl.

7. (Per)haloethers according to claim 1, wherein X$_1$=X$_3$=H and X$_2$=X$_4$=Cl.

8. (Per)haloethers according to claim 1, wherein X$_1$=X$_3$=X$_4$=Cl and X$_2$=H.

9. (Per)haloethers according to claim 1, wherein one of X$_1$, or X$_2$, and/or one of X$_3$ or X$_4$, is/are chosen from the following groups: —COOR$^1_H$, wherein R$^1_H$ is C$_1$-C$_3$ alkyl; —CN; —NCO; —NCS; aryl, substituted with —NO$_2$ or non substituted; and —SO$_2$F.

10. (Per)haloethers according to claim 1, wherein 3a) is C$_1$-C$_5$, linear or branched per(halo)fluorinated alkyl.

11. (Per)haloethers according to claim 1, wherein 3a) is linear or branched (per)fluoroalkyl.

12. (Per)haloethers according to claim 1, wherein 3b) is C$_1$-C$_5$, linear or branched per(halo)fluorinated oxyalkyl, wherein when the alkyl is per(halo), there are one or more atoms of Cl and/or Br.

13. (Per)haloethers according to claim 1, wherein 3b) is linear or branched (per)fluorooxyalkyl.

14. (Per)haloethers according to claim 1, wherein 3a) and 3b) each contain one or more functional groups chosen from: —COOR$^1_H$, wherein R$^1_H$ is C$_1$-C$_3$ alkyl; —OC(O)CH$_3$; —CN; —NCO; —NCS; aryl, substituted with —NO$_2$ or non substituted; —NH—C(O)—NH$_2$; —OC(O)$_2$CH$_3$, —P(O)$_2$(C$_6$H$_5$)$_2$, —P(O)$_2$(C$_6$H$_5$)$_2$, or —SO$_2$F, and/or from fluorinated or hydrogenated organic anhydrides chosen from the group of linear anhydrides of organic $C_1$-$C_4$ mono-carboxylic acids or cyclic anhydrides of $C_4$-$C_6$ dicarboxylic acids.

15. (Per)haloethers according to claim 1, wherein 3a) and 3b) each contain one or more functional groups chosen from: —COOR$^1_H$, wherein R$^1_H$ is $C_1$-$C_3$ alkyl; —OC(O)CH$_3$; —CN; —NCO; —NCS; aryl, substituted with —NO$_2$ or non substituted; —NH—C(O)—NH$_2$; —OC(O)$_2$CH$_3$, —P(O)(C$_6$H$_5$)$_2$, —P(O)$_2$(C$_6$H$_5$)$_2$, or —SO$_2$F, and/or from fluorinated or hydrogenated cyclic anhydrides of $C_4$-$C_6$ dicarboxylic acids.

16. (Per)haloethers according to claim 1, wherein 3c) is $C_1$-$C_5$, linear or branched alkyl, optionally containing one or more functional groups, chosen from: COOR$^1_H$, wherein R$^1_H$ is $C_1$-$C_3$ alkyl; —OC(O)CH$_3$; —CN; —NCO; —NCS; aryl, substituted with —NO$_2$ or non substituted; —NH—C(O)—NH$_2$; —OC(O)$_2$CH$_3$, —P(O)(C$_6$H$_5$)$_2$, —P(O)$_2$(C$_6$H$_5$)$_2$, —SO$_2$F, and hydrogenated organic anhydrides chosen from the group of linear anhydrides of organic $C_1$-$C_4$ mono-carboxylic acids or cyclic anhydrides of $C_4$-$C_6$ dicarboxylic acids; wherein the remaining substituents of the group of $X_1$, $X_2$, $X_3$, $X_4$, independently each from the other, are F, H, Cl or Br.

17. (Per)haloethers according to claim 1, wherein one of $X_1$ or $X_2$, together with one of $X_3$ or $X_4$ and the two carbon atoms of the group -$CX_1X_2$-$CFX_3X_4$ form cyclic fluorinated or hydrogenated anhydride or imide compounds, containing 4 carbon atoms in the ring, wherein the remaining substituents between $X_1$ or $X_2$, and between $X_3$ or $X_4$, have the meanings as defined under 1).

18. (Per)haloethers according to claim 1, wherein X is linear or branched $C_1$-$C_3$ (per)fluoroalkyl, wherein optionally one fluorine atom is substituted with one chlorine atom.

19. (Per)haloethers according to claim 1, wherein when L=1, Rf=Rf' or Rf', the average molecular weight of Rf" is 70 to 3,000.

20. (Per)haloethers of claim 2, wherein when m and n independently one from the other have a value of 0 to 20.

* * * * *